United States Patent [19]

Wilson

[11] Patent Number: 5,703,047
[45] Date of Patent: Dec. 30, 1997

[54] METHODS AND TREATMENTS FOR CORNEAL HEALING WITH GROWTH FACTORS

[75] Inventor: Steven E. Wilson, Plano, Tex.

[73] Assignee: Board Of Regents, The University of Texas System, Austin, Tex.

[21] Appl. No.: 400,323

[22] Filed: Mar. 9, 1995

Related U.S. Application Data

[63] Continuation-in-part of Ser. No. 947,683, Sep. 21, 1992, Pat. No. 5,589,451.

[51] Int. Cl.$^6$ .......................... A61K 38/00; C07K 13/00
[52] U.S. Cl. .......................... 514/12; 500/399; 500/350; 424/85.1
[58] Field of Search .......................... 530/399, 350; 424/85.1; 514/12

[56] References Cited

U.S. PATENT DOCUMENTS 5,032,575  7/1991  Neufeld et al. .......................... 514/12

FOREIGN PATENT DOCUMENTS

PCT/US90/00418  1/1990  WIPO.

OTHER PUBLICATIONS

Stoker et al. Nature 327, pp. 239–242, May 1987.
Marchese et al., J. Cellular Physiology 144:26–332 (1990).
Jacob et al., Eye (1989) 3618–25.
Wilson et al., "EGF, EGF Receptor, Basic FGF, TGF Beta–1, and IL–1 Alpha mRNA in Human Corneal Epithelial Cells and Stromal Fibroblasts," *Investigative Opthalmology &Visual Science*, 33(5):1756–1765, 1992.
Wilson and Lloyd, "Epidermal Growth Factor and Its Receptor, Basic Fibroblast Growth Factor, Transforming Growth Factor Beta–1, and Interleukin–1 Alpha Messenger RNA Production in Human Corneal Endothelial Cells," *Investigative Ophthalmology &Visual Science*, 32(10):2747–2756, 1991.
Dialog Search Report dated Jul. 20, 1992.
Gerdes et al., "Cell Cycle Analysis of a Cell Proliferation-Associated Human Nuclear Antigen Defined by the Monoclonal Antibody Ki–67," *The Journal of Immunology*, 133(4):1710–1715, 1984.
Gerdes et al., "Production of a Mouse Monoclonal Antibody Reactive with a Human Nuclear Antigen Associated with Cell Proliferation," *Int. J. Cancer*, 31:13–20, 1983.
Grant et al., "Effects of Epidermal Growth Factor, Fibroblast Growth Factor, and Transforming Growth Factor–β on Corneal Cell Chemotaxis," *Investigative Ophthalmology &Visual Science*, 33(12):3292–3301, 1992.
Higashiyama et al., "A Heparin–Binding Growth Factor Secreted by Macrophage–Like Cells That Is Related to EGF," *Science*, 215:936–939, 1991.
Kruse and Tseng, "Growth Factors Modulate Clonal Growth and Differentiation of Cultured Rabbit Limbal and Corneal Epithelium," *Investigative Ophthalmology &Visual Science*, 34(6):1963–1976, 1993.

Miyazawa et al., "Molecular Cloning and Sequence Analysis of the cDNA for a Human Serine Protease Responsible for Activation of Hepatocyte Growth Factor," *The Journal of Biological Chemistry*, 268(14):10024–10028, 1993.
Nakamura et al., "Requirement of Microtubule Assembly for Initiation of EGF–Stimulated Corneal Epithelial Migration," *Jpn. J. Ophthalmol.*, 35:377–385, 1991.
Nishida et al., "Differential Modes of Action of Fibronectin and Epidermal Growth Factor on Rabbit Corneal Epithelial Migration," *Journal of Cellular Physiology*, 145:549–554, 1990.
Ohashi et al., "Presence of Epidermal Growth Factor in Human Tears," *Investigative Ophthalmology &Visual Science*, 30(8):1879–1882, 1989.
Sambrook et al., "Molecular Cloning," 2nd ed., Cold Spring Harbor Laboratory Press, 1989.
Schermer et al., "Differentiation–related Expression of a Major 64K Corneal Keratin In Vivo and In Culture Suggests Limbal Location of Corneal Epithelial Stem Cells," *The Journal of Cell Biology*, 103:49–62, 1986.
Tsutsumi et al., "Epidermal Growth Factor–like, Corneal Wound Healing Substance in Mouse Tears," *The Journal of Clinical Investigation, Inc.*, 81:1067–1071, 1988.
Wilson et al., "Fibroblast Growth Factor Receptor–1 Messenger RNA Expression in Corneal Cells," *Cornea*, 12:249–254, 1993.
Wilson et al., "Hepatocyte Growth Factor, Kerationocyte Growth Factor, Their Receptors, Fibroblast Growth Factor Receptor–2, and the Cells of the Cornea," *Investigative Ophthalmology &Visual Science*, 34(8):2544–2561, 1993.
Wong et al., "The TGF–α Precursor Expressed on the Cell Surface Binds to the EGF Receptor on Adjacent Cells, Leading to Signal Transduction," *Cell*, 56:495–506, 1989.
Zieske et al., "α–Enolase Is Restricted to Basal Cells of Stratified Squamous Epithelium," *Developmental Biology*, 151:18–26, 1992.
Zieske et al., "Characterization of a Potential Marker of Corneal Epithelial Stem Cells," *Investigative Ophthalmology &Visual Science*, 33(11):143–152, 1992.

*Primary Examiner*—Cecilia J. Tsang
*Assistant Examiner*—P. Lynn Touzeau
*Attorney, Agent, or Firm*—Arnold, White & Durkee

[57] ABSTRACT

The invention relates to the use of hepatocyte and keratinocyte growth factors for stimulating the proliferation and motility of corneal cells in vivo and in vitro. Also disclosed is the use of these factors for maintaining the viability of corneal cells during or after ocular surgery and during corneal preservation in storage medium prior to transplant. Polymerase chain reaction amplification has demonstrated that corneal epithelial and endothelial cells in vitro and ex vivo corneal epithelium produce messenger RNA coding for hepatocyte growth factor, hepatocyte growth factor receptor, keratinocyte growth factor, and keratinocyte growth factor receptor. Several growth factors were found to inhibit the differentiation of corneal epithelial cells as measured by decreased expression of keratin K3. Methods for treating ocular dry eye diseases are presented.

11 Claims, 15 Drawing Sheets

METHODS AND TREATMENTS FOR CORNEAL HEALING WITH GROWTH FACTORS

This is a continuation-in-part of U.S. patent application Ser. No. 07/947,683 filed Sep. 21, 1992 now U.S. Pat. No. 5,589,451, the entire text of which is herein incorporated by reference without disclaimer.

The United States Government has certain rights in the invention pursuant to the terms of grant EY 09389 awarded by the National Institutes of Health.

BACKGROUND OF THE INVENTION

1. Field of the Invention

The invention relates to methods of preservation and healing of corneal tissue and to treatment of eye diseases arising from a deficiency in the coating of the ocular surface with mucins and tears. Compositions for these treatments are also disclosed.

2. Description of Related Art

Corneal wound healing and the many factors which may promote or prevent it, have been of concern to both clinicians and researchers. Ophthalmologists are frequently confronted with corneal dystrophies and problematic injuries that result in persistent and recurrent epithelial erosion, often with permanent endothelial loss. Attempts have been made to use growth factors to stimulate healing of the corneal epithelium and endothelium following injury or surgery. However, only a limited number of approaches are currently available for treating patients who fail to heal epithelial injuries adequately.

Epidermal growth factor (EGF) is one substance that has been investigated as a means to stimulate the healing of corneal epithelium and endothelium following injury or surgery. This factor has also been tested as a storage media for corneal preservation in efforts to improve the viability of corneal endothelial cells following corneal storage. However, there is yet no convincing evidence that EGF is effective for healing or stimulating corneal epithelial cell growth. The majority of the available in vitro and in vivo studies on corneal tissue have been performed with epidermal growth factor (EGF); e.g., to attempt to stimulate the healing of the corneal epithelium and endothelium following injury or surgery, or to store media used for corneal preservation in attempts to improve the viability of corneal epithelial and endothelial cells following corneal storage.

In some animal studies, EGF has exhibited some activity toward corneal cells. Epidermal growth factor has been shown to stimulate the proliferation of bovine corneal epithelial cells in vitro (Gospodarowicz, et al., 1977). Similarly, in vivo animal studies have shown that epidermal growth factor stimulates corneal epithelial wound healing in the rabbit (Soong, et al., 1989) and rat (Brazzell, et al., 1991); Kitazawa, et al., 1990); Chung and Fagerholm, 1989; Reim, et al., 1988) after superficial epithelial wounding, keratectomy wounds of the anterior corneal surface, and corneal alkali burns. In two of these studies, however, there was increased vascularization (Chung and Fagerholm, 1989) and increased inflammatory response (Reim, et al., 1988) in the epidermal growth factor treated corneas compared with the control corneas. One randomized prospective trial of epidermal growth factor for the treatment of epithelial wounds (Kandarakis, et al., (1984)) demonstrated no difference between epidermal growth factor and vehicle alone in the rate of corneal epithelial wound healing after penetrating keratoplasty. Thus, despite the fact that epidermal growth factor has been available for over a decade, in vivo randomized trials have not demonstrated that epidermal growth factor stimulates corneal epithelial wound healing compared with controls.

Efforts to use EGF to promote corneal endothelium healing or to preserve corneal cells have also been without much success. EGF stimulates in vitro proliferation or migration of bovine endothelium (Gospodarowicz, et al., 1977; Junquero, et al., 1990 and rabbit Raymond, et al., 1986; Joyce, et al., 1989). Similarly, epidermal growth factor stimulates the in vitro proliferation of human corneal endothelial cells (Nayak, et al., 1984). The use of epidermal growth factor in corneal preservation and intraocular use during eye surgery have been proposed (Neufeld, A.H., 1991). In two independent studies, however, epidermal growth factor did not stimulate the healing of cat corneal endothelium in vivo when epidermal growth factor was injected into the eye after cold-induced injury (Rich, et al., 1991; Brogdon, et al., 1989). A disappointing result was recently shown in a masked, randomized, prospective, multicenter trial in which paired corneas from the same donor were preserved in identical corneal preservation media with or without epidermal growth factor. There was no difference in the corneal endothelial cell counts between the epidermal growth factor and control groups at one or two years of follow-up.

The negative results obtained with EGF-stimulated corneal epithelial wound healing and corneal endothelial preservation in randomized prospective trials highlight a lack of other more effective agents to stimulate corneal epithelial and endothelial proliferation and preservation after wounding or during corneal preservation.

The functional status of the endothelium and sustained corneal deturgescence after corneal preservation are clinically important and are primary goals in the development of corneal storage media. Desirable storage characteristics include the extension of corneal preservation time, enhancement of corneal wound healing, and the reduction of normal progressive loss of endothelial cells post keratoplasty. In preserving corneas for transplants, for example, it is important that the endothelial cells remain viable and metabolically active and able to change to a mitotically active state after implantation.

The work reported so far indicates the need to develop compositions that have a beneficial effect on corneal wound healing. While some studies indicate that EGF may have a beneficial effect in promoting epithelial cell proliferation, its effect on endothelial cell viability is problematic. Healing and preservation of both epithelial and endothelial cells is important because endothelial cell viability and function is fundamentally important in maintaining corneal clarity and vision during the aging process as well as after disease, surgery, or laser treatments. One problem of particular concern is the commonly encountered condition associated with dry eye diseases. The dry eye syndrome typically manifests in severe, debilitating ocular discomfort, leading in some cases to decreased vision due to irregularity of the corneal surface. In severe cases, there may be loss of the eye.

Certain groups of individuals are susceptible to keratoconjunctivitis sicca, known as dry eye syndrome. The condition may arise as a consequence of aging, especially in females, and in patients with rheumatologic diseases such as Sjögren's Syndrome or rheumatoid arthritis. Clinical signs of this often debilitating ocular disorder include Rose bengal staining of the ocular surface, tear film instability and increased tear osmolality (van Bijsterveid, 1969; Bron et al, 1994). However, decreased tearing is not always observed. It is a well known clinical phenomenon that many patients diagnosed with keratoconjunctivitis sicca on the basis of symptoms do not actually have evidence of a deficiency in the amount of tears (van Bijsterveid, 1969; Bron et al, 1994). Unfortunately, there is no universally accepted treatment that is effective. Keratoconjunctivitis sicca is usually treated the same in all patients by use of artificial tears and ointments even when there is evidence of sufficient tears. The results of these treatments are variable, and are often unsatisfactory.

Other dry eye ocular surface diseases suffer from the lack of an effective treatment regimen. These diseases include Sjögren's disease, trachoma and erythema multiforme.

At present, only a limited number of approaches are available for treating patients who fail to heal either epithelial or deep wound injuries involving endothelial cell structure, or can be effectively treated for dry eye ocular surface diseases.

SUMMARY OF THE INVENTION

The present invention relates to compositions and methods employing particular growth factors that successfully maintain corneal cell viability and promote corneal cell proliferation. Useful compositions include growth factors that are produced in corneal epithelial, endothelial, and lacrimal cells. The methods are appropriate for treatment of corneal injury subsequent to accidental injury, surgical procedures affecting the cornea, and disorders of the cornea in which there are abnormalities of the normal healing process of the epithelium and endothelium. The disclosed compositions are suitable for improving the viability of the corneal epithelium and endothelium during corneal preservation prior to transplantation of the cornea. Certain growth factors also been found to be beneficial for treating dry eye ocular conditions such as keratoconjunctivitis sicca. For these treatments, growth factors appropriate for use include generally those that inhibit differentiation of human corneal cells by suppressing keratin K3 and other keratin formation in corneal epithelial cells.

In certain embodiments, the inventor has discovered that keratinocyte and hepatocyte growth factors are surprisingly effective in promoting corneal cell proliferation. Previous studies had reported that HGF was stimulatory for repair of liver tissue and for enhancing proliferation of some types of cells such as human keratinocytes. However, it was only after the inventor's discovery that hepatocyte growth factor, hepatocyte growth factor receptor, keratinocyte growth factor, and keratinocyte growth factor receptor were produced in human corneal epithelial cells, keratinocytes and corneal endothelial cells that a role for these growth factors in regulating normal functions in human corneal epithelial cells and corneal endothelial cells was contemplated. Once HGF and KGF RNA were detected in corneal tissue, the inventor went further to demonstrate that exogenous hepatocyte growth factor and keratinocyte growth factor stimulated the proliferation of human corneal epithelial cells and human corneal endothelial cells. Surprisingly, both EGF and KGF stimulated corneal cells more efficiently than EGF. Even more unexpected was a dose response corneal cell stimulation within a range up to about 50 ng/ml, with subsequent inhibition at higher concentrations.

The present invention also relates to methods of treatment employing hepatocyte and keratinocyte growth factor in promoting or regulating the healing or viability of corneal tissue following injury to the cornea or for any disorder of the ocular surface. The method involves treatment of corneal cells with an effective amount of hepatocyte growth factor in a pharmaceutically acceptable composition. This method is appropriate for treating both superficial and deep wounds; for example, wounds that affect either epithelial or endothelial cells. Such injuries include injuries to epithelial cells, corneal keratocyte cells populating corneal center regions, and corneal cells located on the corneal posterior surface.

Specific disorders typically associated with epithelial cell damage and for which the disclosed compositions provide beneficial treatment include persistent corneal epithelial defects, recurrent erosions, neurotrophic corneal ulcers, keratoconjunctivitis sicca, microbial corneal ulcers, viral cornea ulcers, and the like. Surgical procedures typically causing injury to the epithelial cell layers include laser procedures performed on the ocular surface, any refractive surgical procedures such as radial keratotomy, photoreactive keratectomy and astigmatic keratotomy, conjunctival flaps, conjunctival transplants, epikeratoplasty, and corneal scraping.

Pharmaceutically acceptable compositions of HGF or KGF may be applied topically to the ocular surface, either alone or in combination with other drug delivery systems; for example, in a hyaluronic acid solution or suspensions of collagen fragments. Particular formulations may be in the form of liquids, suspensions, ointments, complexes to a bandage collagen shield, or the like.

Pharmaceutically acceptable compositions of either KGF or HGF may be modified by the addition of the other growth factor. Thus, in a particular embodiment of a method for promoting corneal cell proliferation, both hepatocyte growth factor and keratinocyte growth factor may be included in pharmaceutically accepted compositions. Preferred compositions for corneal endothelial cell proliferation will generally employ relatively narrow concentration ranges of the growth factors. The range for optimal activities is between less than one nanogram up to about 50 nanograms per milliliter, as indicated from in vitro experiments on endothelial and epithelial corneal cells. A preferred concentration is about five to about ten nanograms per milliliter for either hepatocyte or keratinocyte growth factor-promoted stimulation of corneal cells. Higher concentrations, pu to 100 times these levels may be applied by topical formulations to yield a localized concentration of 5 to 10 ng/ml at the cell surface.

Hepatocyte and keratinocyte growth factors are also useful in promoting healing of the corneal endothelium. This is particularly valuable for deep wound injury to the cornea in which the endothelium is significantly disrupted, such as following surgical procedures performed on the anterior segment of the eye or for disorders of the cornea in which there are abnormalities of the corneal endothelium. Examples of such disorders include Fuchs' endothelial dystrophy, aphakic bullous keratopathy, pseudophakic bullous keratopathy, endothelial graph rejection, viral endotheleitis, iritis, and so forth.

KGF and HGF will also be useful in maintaining the viability or increasing the cell density of corneal endothelium following any surgical procedure performed on the anterior segment of the eye, such as cataract surgery, penetrating keratoplasty, intraocular lens insertion, intraocular lens exchange, iridoplasty, pupiloplasty, trabeculectomy, and so forth. In like manner, compositions containing HGF or KGF may be useful for preserving corneal tissue just prior to ocular surgery.

Also included in the invention are compositions useful for the preservation of corneal tissue. These compositions will contain an appropriate amount of hepatocyte or hepatocyte-like growth factor, optionally including keratinocyte or keratinocyte-like growth factor, in a tissue-compatible physiologically acceptable composition. A preferred amount of keratinocyte growth factor or hepatocyte growth factor to be used in these compositions will generally be between about one and about fifty nanograms per milliliter of each factor. However, amounts up to about 50 ng/ml may be useful in some applications where extensive proliferation is desired. Concentrations higher than about 50 ng/ml are typically found to be inhibiting; otherwise, up to about 50 ng/ml there is a dose response proliferation. One may desire to initiate proliferation with the appropriate dose, then inhibit proliferation by adding KGF or HGF until an inhibitory concentration is reached. Reinitiation of proliferation could be performed, for example, by dilution.

Compositions comprising keratinocyte and/or hepatocyte growth factor for several applications of in vivo treatment of human corneal disorders are also contemplated as part of the present invention. Where large amounts of epithelial tissue are destroyed the compositions are preferably administered topically. Administration may be in the form of a liquid, suspension, ointment, combination with a visco elastic agent or the like. Where extensive epithelial damage occurs, for example, the compositions may be administered intradermally or possibly subcutaneously, and this may be viewed as an internal topical administration.

The invention therefore is directed to compositions which include one or both of hepatocyte or keratinocyte growth factors and further to pharmaceutical compositions which include a pharmaceutically acceptable carrier. Suitable pharmaceutical carriers include, sterile aqueous solution, various organic solvents, emulsifying or suspending agents, or aqueous diluents such as water, ethanol, propylene glycol, glycerin or combinations thereof. Ophthalmic solutions for topical administration would be administered to the eye of the subject in need of treatment in the form of an ophthalmic preparation prepared in accordance with conventional pharmaceutical practice, see, for example, "Remingtons Pharmaceutical Sciences" 15th Ed., pg. 1488–1501 (Mac Publishing Co., Easton Pa.).

Ophthalmic preparations will contain one or both of the growth factors HGF or KGF, or pharmaceutically acceptable salts thereof in a usually preferred concentration of about one to fifty nanograms per milliliter for stimulating corneal cell proliferation or corneal preservation. In many cases, about five to ten nanograms per milliliter will be preferred. Stimulation by as little as 1 ng/ml may also be appropriate where less extensive proliferation is desired. Where the compositions are designed for use in treating dry eye diseases, amounts on the order of 5–10 ng/ml applied at the cell surface would be appropriate, adjusted for severity of the disease to be treated and the patient, e.g., pediatric or geriatric such that lesser or greater amounts might be appropriate or of course within the range recited such as 6,7,8 or 9 ng/ml. In a pharmaceutically acceptable solution, suspension, or ointment some variation in concentration will necessarily occur depending on the particular combination of growth factors employed, the condition of the subject to be treated and so forth. The person responsible for treatment will determine the most suitable concentration for the individual subject. Ophthalmic preparations will preferably be in the form of a sterile aqueous solution containing, if desired, additional ingredients, for example, preservative, buffers, tenacity agents, antioxidants, stabilizers, non ionic wetting or clarifying agents, viscosity increasing agents and the like. Additionally, other beneficial compounds may be added, such as cytokines, hormones or growth promoting agents.

Suitable preservatives for use in such a solution include benzalkonium chloride, benzethonium chloride, chlorobutanol, thimerosal, and the like. Suitable buffers include boric acid, sodium and potassium bicarbonate, sodium and potassium borates, sodium and potassium carbonate, sodium acetate, sodium biphosphate and the like, in amounts sufficient to maintain the pH between about pH 6 and pH 8, preferably between about pH 7 and pH 7.5. Suitable tonicity agents are dextran 40, dextran 70, dextrose, glycerine, potassium chloride, propylene glycol, sodium chloride, and the like such that the sodium chloride equivalent of the ophthalmic solution is in the range of 9.9 plus or minus 0.2%. Suitable antioxidant and stabilizers include sodium bisulfite, sodium metabisulfite, sodium thiosulfate, thiourea and the like. Suitable wetting and clarifying agents include polysorbate 80, polysorbate 20, poloxamer 282, and tyloxapol. Suitable viscosity increasing agents include dextran 40, dextran, 40, gelatin, glycerin, hydroxyethyl cellulose, hydroymethylpropyl cellulose, lanolin, methylcellulose, petrolatum, polyethylene glycol, polyvinyl alcohol, polyvinyl polyvinylpyrrolidone, carboxymethyl cellulose and the like. The ophthalmic preparation will be administered topically to the eye of the subject in need of treatment by conventional methods. For example, in the form of drops or by bathing the eye in the ophthalmic solution.

While certain aspects of the invention have been illustrated with keratinocyte and/or hepatocyte growth factor, it will be recognized that any active segment or compound with KGF or HGF-like properties may be substituted. One might identify and select suitable compounds, for example, by their binding affinities toward corneal cell receptors for HGF and KGF.

The source of any of the growth factors, i.e. KGF, EGF, DC-HGF, HB-EGF or TGF alpha, may be from natural sources, by synthesis or by production in recombinant cells. Active fragments may also be used. Some of these compounds are likely to be more effective than the intact factors and in such cases one may expect optimal amounts to differ somewhat from the preferred range herein demonstrated for the intact factors.

In yet another aspect of the invention, compositions containing one or both HGF or KGF may be used to modulate corneal cell proliferation. It has been found that above about 50 ng/ml, HGF or KGF inhibits corneal cell proliferation. Thus, it is contemplated that one might attenuate corneal cell proliferation as desired attenuated by altering the concentration of HGF or KGF.

The invention also includes methods particularly for treating dry eye ocular surface diseases, particularly keratoconjunctivitis sicca or dry eye syndrome. Generally the eye is treated with a composition that prevents conditions leading to decreased coating of the ocular surface with mucins and tear film. The inventor has discovered that overdifferentiation of corneal epithelial cells is associated with high expressed levels of keratins that prevent formation of protective mucus and tear films on the eye. Such overdifferentiation is inhibited with several types of growth factors, including HGF, EGF, heparin-binding EGF and TGF alpha for example. Of course other growth factors, so long as keratin expression is inhibited, are also contemplated to be useful. Molecules that bind at the active site of the respective growth factor receptors would also be expected to be effective. Such "designer" molecules would be constructed from structural knowledge of the active site.

As a convenience, active drug may be applied so as to be released over a period of time, such as from encapsulation in polymeric microcapsules suitable for use in the eye, or implanted on the ocular periphery to release into the tear film. One prefers biodegradable microcapsules for such use, such as drug encapsulated in polyglutamate microcapsules. Techniques for such preparations are well known. Microcapsulation of drugs in microcapsules ranging from 1 to several hundred μ is described for example in U.S. Pat. No. 5,238,714 (Aug. 24, 1993) incorporated herein by reference in the entirety. Time release capsules may be implanted into the focrices of the eye or into the orbit subconjunctivally. The size should be large enough to retain at least a day's supply of growth factor, but small enough to not be detected by the patient doing blinking. A continuous delivery vehicle that would have a minimum of 24 hours would be preferred, although shorter times are also contemplated to be useful.

In particular applications, as in keratoconjunctivitis sicca, the patient will preferably be treated with topical applications of growth factors such as HGF, EGF, heparin binding EGF or TGF alpha in a pharmaceutically acceptable composition. As known to those skilled in matters of determining appropriate dosages, the amount of active components employed may be tailored to contemplated use of the formulations and to the age and medical condition of the patient. For general use, dosages in the range of 50–100 ng/ml will be appropriate, preferable applied topically as for example eyedrops several times daily or as needed. For long term treatment, timed release subcutaneous implants may be employed such as collagen matrices or small bits of porous devices that contain active ingredient released through the pores over time, e.g., zeolites, carrageenans, and the like.

Compositions including double-chain HGF, EGF, heparin binding EGF or TGF alpha are also effective for restoring ocular surface mucin coating. Treatment regimens would be similar to those used with dry eye ocular conditions. The effect of abnormal or lack of mucin coating may frequently be associated with dry eye syndrome and would be treated concurrently.

In some eye conditions, it may be desirable to inhibit keratin K3 expression. Compositions similar to those disclosed for treatment of dry eye ocular conditions would be useful in this respect. Of course somewhat different treatment strategies may be needed, such as timing of administration, and the differing effects of the individual growth factors. Particular formulations may be more appropriate for an individual, for example, pediatric or geriatric application.

It is contemplated that any of the particular growth factors found to be effective in treating dry eye ocular diseases, or in inhibiting keratin K3 expression, may be used separately or in combination with each other. This would involve selection of any of EGF, HB-EGF, TGF alpha or DC-HGF and combinations of these. Of course, as discussed, active segments of these factors would be equally useful as would specific molecules designed to fit the receptors of the respective factors. Such tailored molecules need not be polypeptides and might for example be nitrogen heterocycles, organic chelates or polycyclic compounds.

DETAILED DESCRIPTION OF PREFERRED EMBODIMENTS

Figure 1A:
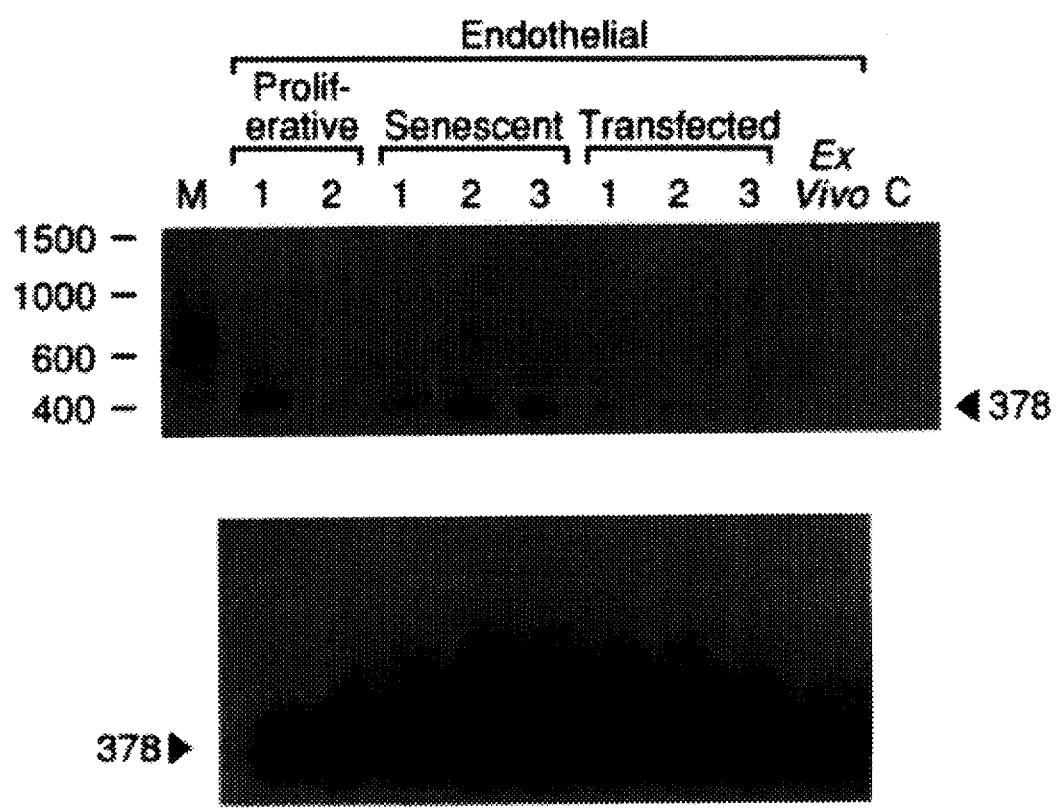
FIG. 1A. Ethidium bromide-stained agarose gel of hepatocyte growth factor PCR-amplified products that were amplified using the hot start method from the cDNA samples generated from human cells. Shown are primary proliferative endothelial cells, primary senescent endothelial cells, SV40 large T antigen-transfected endothelial cells and ex vivo endothelium.

The effects of exogenous epidermal growth factor (EGF), heparin-binding EGF (HB-EGF), transforming growth factor alpha (TGF alpha), single-chain precursor hepatocyte growth factor (SC-HGF), double-chain mature HGF (DC-HGF), and keratinocyte growth factor (KGF) on proliferation, motility, and differentiation of human corneal epithelial cells in vitro have been determined. Proliferation, motility, and differentiation of corneal epithelial cells was studied using first passage cultures of human corneal epithelial cells in serum-free chemically defined medium. The effect of EGF, HB-EGF, SC-HGF, DC-HGF, KGF, or combinations of the growth factors on proliferation was measured by counting cells present after 3 weeks of culture and by immunostaining for the cell cycle-specific nuclear proliferation antigen Ki-67.

The effect of the factors on epithelial cell motility was assessed by morphometric analysis of photographs of cells migrating from confluent islands of cells. The effect of growth factors on differentiation of epithelial cells was determined by immunostaining epithelial cell islands for the keratin K3 and by Western blotting for keratin K3. EGF, alone or in combination with KGF and SC-HGF, significantly stimulated motility of epithelial cells at the periphery of confluent islands of cells and induced an elongated cell morphology. TGF alpha, HB-EGF, and DC-HGF produced motility effects similar to EGF.

There was diminished proliferation of the migrating cells in response to EGF, HB-EGF, TGF alpha, or DC-HGF, while non-migrating epithelial cells in the center of confluent islands continued to proliferate in response to the growth factors. EGF, HB-EGF, TGF alpha, or DC-HGF inhibited expression of the differentiation-related marker keratin K3 in epithelial cells, both at the edge and at the center of the islands. KGF stimulated proliferation of corneal epithelial cells at low density and in confluent islands of cells. KGF did not affect expression of keratin K3 or migration of epithelial cells. SC-HGF had no effect on corneal epithelial cells.

These results indicate that the effects of EGF, HB-EGF, TGF alpha, and DC-HGF on corneal epithelial cell proliferation, motility and differentiation vary from those of KGF and SC-HGF. EGF, HB-EGF, TGF alpha, and DC-HGF induced changes in epithelial cell morphology and motility occur in cells plated at low cell density or in cells located at the edge of a confluent island. These effects appear to be dependent on the extent of cell-cell contact. The inhibitory effect of EGF, HB-EGF, TGF alpha, or DC-HGF on corneal epithelial cell differentiation, however, is independent of cell density. In contrast, KGF stimulates proliferation of human corneal epithelial cells regardless of the cell density, does not significantly affect motility, and has no effect on differentiation in serum-free defined medium in vitro.

Two growth factors, keratinocyte growth factor and hepatocyte growth factor, have been previously characterized. These growth factors are naturally occurring substances that appear to have a role in controlling such functions as development, growth, motility, and viability of cells that produce the specific receptors for the growth factors. Keratinocyte growth factor is a member of the fibroblast growth factor family that was originally isolated from human embryonic lung fibroblast-conditioned medium (Rubin, et al., 1989). Keratinocyte growth factor stimulates the proliferation of keratinocytes [skin epithelial cells] (Marchese, et al., 1990), but has no effect on several lines of fibroblasts (Rubin, et al., 1989). High affinity keratinocyte growth factor receptors have been identified on Balb/MK keratinocytes, but not on NIH/3T3 fibroblasts (Bottaro, et al., 1990).

Hepatocyte growth factor is active in the repair of liver tissue (Monteasano, et al., 1991). It is identical to the scatter factor which stimulates the dissociation and scattering of epithelial cells (Gherardi and Stoker, 1990). Hepatocyte growth factor stimulates cell proliferation in such cell types as melanocytes and vascular endothelial cells (Rubin, et al., 1991). Hepatocyte growth factor has been shown to stimulate proliferation and migration of human keratinocytes (Matsumoto, et al., 1991). Hepatocyte growth factor receptor has been identified as the c-Met proto-oncogene product and has been detected in certain types of epithelial cells (Bottaro, et al., 1991; Prat, et al., 1991).

The present invention relates to methods and therapeutic compositions useful in corneal wound healing and preservation of corneal tissue. The compositions include hepatocyte and keratinocyte growth factor, neither of which has previously been associated with corneal tissue. The inventor has discovered that KGF and HGF may be used to induce corneal cell proliferation. This discovery resulted from experiments showing that KGF and HGF mRNA were present in corneal cells. Work by others had demonstrated the presence of HGF mRNA in vascular endothelial cells and liver Kupffer cells, but neither HGF nor KGF had been demonstrated in corneal cells. Once the presence of HGF and HGF in corneal cells was detected, the inventor determined that either or both of these factors stimulated corneal cell proliferation in a dose response manner. Moreover, such stimulation was effective at lower concentrations than EGF.

Generally, damage to corneal tissue, whether by disease, surgery or injury, may affect epithelial and/or endothelial cells, depending on the nature of the wound. Corneal epithelial cells are the non-keratinized epithelial cells lining the external surface of the cornea and provide a protective barrier against the external environment. Superficial wounds such as scrapes, surface erosion, inflammation, etc. mainly affect this type of cell. Endothelial cells, on the other hand, are found lining the internal surface of the cornea and most often are damaged by specific internal disorders, wounds to the posterior region of the cornea. Corneal endothelial cells maintain the clarity of the cornea by continually pumping water from the cornea into the anterior chamber of the eye.

The effects of exogenous HGF, KGF and EGF on the proliferation of cultured human corneal epithelial, stroma fibroblast and endothelial cells were compared. In each case, first passage cells from donors less than one year of age were plated in culture plates. Corneal epithelial cells, stroma fibroblast and corneal endothelial cells were plated in the wells for two days in an appropriate medium without KGF or HGF. The various growth factors were added individually and after five days of incubation, cells were trypsinized to complete dissociation and the number of cells in each well determined. The results showed that HGF and KGF significantly stimulated the in vitro proliferation of corneal epithelial cells and corneal endothelial cells. For both epithelial and endothelial cells, HGF or KGF significantly stimulated proliferation at a lower concentration than EGF. Moreover, HGF or KGF required a lower concentration than EGF to produce significant stimulation (see FIGS. 5–8). All three factors, HGF, KGF, or EGF, exhibited a decreased endothelial cell stimulatory effect at concentrations greater than about 50 ng/ml. This discovery indicated that corneal cells were stimulated by concentrations of about 1 to about 50 ng/ml but that at higher concentrations, inhibitory effects occurred.

Surprisingly, the inventor also found that TGF alpha, DC-HGF, EGF and HB-EGF stimulated proliferation and inhibited K3 expression. Growth factors had previously been reported in murine tears (Tsutsumi, et al, 1988) and human tears (Okashi, 1989) but no connection between their presence and the participation of lacrimal tissue in ocular surface maintenance was made. For the first time, a treatment is now available for treatment of dry eye ocular diseases now that the relationship between the production of growth factors and their interaction with exocrine pathways in corneal and conjunctival epithelial cells has been brought to light.

The following examples illustrate the practice of the present invention and are not intended to be limiting. It will be recognized that numerous clinical applications of the keratinocyte and hepatocyte growth factors compositions are indicated, including in vivo and in vitro use, as mentioned previously herein.

The examples show that keratinocyte growth factor (KGF) and hepatocyte growth factor (HGF) are unexpectedly beneficial in corneal endothelial and epithelial cell wound healing and stimulate corneal cell proliferation at lower concentrations than EGF. The examples also provide support for the use of HGF, EGF, HB-EGF and TGF alpha in treating dry eye ocular disorders.

Materials and Methods

HUMAN CORNEAL EPITHELIAL CELL CULTURES: Primary cultures of human corneal epithelial cells were established by a previously described method using cadaveric corneas obtained from eye banks involving separation of the epithelial cells by dispose digestion (Wilson, He, and Lloyd, 1992b). Cultures generated from different donors were utilized in each experiment. IN the opinion the study was performed in accordance with the principles of the Helsinki Accord on Human Rights. All experiments on the effects of exogenous growth factors on proliferation, migration, and differentiation were conducted with first passage corneal epithelial cells.

PROLIFERATION ASSAYS: Proliferation experiments were performed by plating $1\times10^6$ cells/flask in Costar (Cambridge, Mass.) 25 cm$^2$ flasks in 3 ml of Keratinocyte Defined Medium (KDM, modified MCDB 153, 5 µg/ml insulin, 0.5 µg/ml hydrocortisone, 0.15 mM $Ca^{2+}$, without EGF, Clonetics, San Diego, Calif.) without growth factors, serum, or other extracts. Twenty four hours after seeding the cells, growth factors were added to the medium. Growth factors were diluted in sterile PBS with 0.2% gelatin at the time of addition so that 5 µl of additional volume was added to each well to give the final concentration of growth factor. Each growth factor or combination of growth factors was tested in three flasks in each experiment. Five µl of PBS with 0.2% gelatin as vehicle was added to control flasks. Media were changed at 3 day intervals with the addition of new growth factors. Cells were photographed with an inverted phase contrast microscope, washed once, and dissociated to single cells with 1 ml of 0.25% trypsin (approximately 10 minutes). The total number of cells for each well was determined from the average of 3 counts made with a Coulter counter (Model $Z_f$, Hialeah, Fla.). Errors were expressed as the standard error of the mean. Statistical comparisons were performed with the Newman-Keuls nonparametric test, a standard test for studies in which comparisons are made between differing experimental groups and a control group (Zar, 1984). A z value less than 0.05 was considered statistically significant.

GROWTH FACTORS: Human EGF was obtained from three different commercial sources and different stock solutions form each supplier were tested: Collaborative Biomedical Products, (Bedford, Mass.), Clonetics (San Diego, Calif.), and Sigma Chemical Co. (St. Louis, Mo.). Recombinant heparin-binding EGF (HB-EGF) was provided by Scios Nova (Mountain View, Calif.). Recombinant human TGF alpha was provided by Brystol-Myers Squib (Seattle, Wash.). EGF, HB-EGF, and TGF alpha were tested at 10 ng/ml (Wilson et al., 1993). Human KGF was from Bachem (Philadelphia, Pa.). For cell proliferation assays a preparation of HGF that contained a mixture of both single-chain and double-chain HGF (SCDC-HGF) was obtained from Collaborative Biomedical Research (Bedford, Mass.). Subsequent lots of HGF from Collaborative Biomedical Research containing pure single-chain (SC-HGF) were used in cell migration experiments. Human recombinant double-chain HGF (DC-HGF) obtained from Genentech, Inc. (San Francisco, Calif.) was used in cell proliferation, migration, and immunostaining experiments. Human HGF and KGF were tested at 5 ng/ml (Wilson et al., 1993). Stock solutions of the growth factors were aliquoted into siliconized microtubes and stored at −80° C. to minimize denaturation due to repeated thawing prior to use.

CELL MIGRATION ASSAY: The effects of the growth factors on migration of corneal epithelial cells were evaluated using confluent islands of cells grown in Costar six-well plates. Two ml of KDM were placed into each well and a 1 cm diameter cloning cylinder was placed in the center of the well without any adhesive. One hundred μl of KDM containing $1 \times 10^5$ primary human corneal epithelial cells were added to the central well of the cloning cylinder. After 24 hours of culturing, the cloning cylinder was removed and non adherent cells we washed from the well. This technique produced a 1 cm diameter central region of confluent epithelial cells. The perimeter of each island of cells (origin) was delineated on the plastic with a marker prior to adding growth factors. Growth factors were added in 2 ml of fresh KDM. Cells were monitored and fresh KDM and growth factors were added at 3 day intervals. The cells at the center and the margin of the cell patch in each flask were photographed with an inverted phase contrast microscope at the termination of the experiment. Migration experiments extended for 14–18 days.

IMMUNOCYTOLOGIC STAINING: Immunostaining was performed directly on the cells in the six well plates. Briefly, cells were washed with phosphate buffered saline (PBS) and fixed with 1% paraformaldehyde in pH 7.2 phosphate buffer for 2 minutes. After three washes of 5 minutes each with PBS, cells were extracted for 3 minutes with acetone at −20° C. Cells were rehydrated for 3 minutes in PBS and nonspecific binding sites were blocked with goat serum diluted 10-fold in PBS. Cells in individual wells were exposed for 40 minutes to AE5 monoclonal antibody to keratin K3 (Schermer, Galvin, and Sun, 1986) diluted 100-fold (a gift from T-T Sun) or DAKO-Ki-67 monoclonal antibody (Dako A/S, Glostrup, Denmark) which reacts with a nuclear antigen expressed on all human proliferating cells (Gerdes et al., 1983). The reactive antigen is expressed during $G_1$, S, $G_2$, and M phases of mitosis, while cells in $G_0$ consistently lack the Ki-67 antigen (Gerdes et al., 1984). After three washes with PBS, cells were exposed to goat anti-mouse IgG labeled with fluorescein. Secondary antibody solutions also contained rhodamine phalloidin at a 4-fold dilution. After three final washes with PBS, cells were mounted with a glass coverslip using 50% glycerol in PBS containing a crystal of phenylenediamine. Photographs were taken with a fluorescent microscope using a 25X objective lens that fit into the well of the six-well plate. Exposure times for AE5 stained sections was a constant 10 seconds for each growth factor or combination of growth factors.

QUANTITATION ON MOTILITY: After the fluorescence image was photographed, coverslips were floated off with PBS and cells were stained with 1% methylene blue for 5 minutes. Cells were washed 3× with PBS, dried, and photographs of individual wells taken with a 35 mm camera and a 70 mm lens. The areas of three central islands for the control or growth factor were averaged in each experiment and expressed as percent of control. Statistical comparisons were performed between growth factors and controls using the results of three experiments and the Newman-Keuls method (Zar, 1984).

WESTERN BLOTTING: Western blotting was performed as described previously with the 4G10.3 monoclonal antibody to enolase (Zieske, Bukusoglu, and Yankauckas, 1992) and the AE5 monoclonal antibody (Schermer, Galvin, and Sun, 1986). Briefly, T-25 flasks of first passage human corneal epithelial cells in KDM that were approximately 80% confluent were utilized. Cultures incubated with vehicle (control, 3 flasks), EGF 10 ng/ml (3 flasks), or KGF 5 ng/ml (3 flasks) were maintained for one or two weeks with changes in medium and growth factors at 3 day intervals. HGF was not included in the Western blotting experiments due to the prohibitive expense of the growth factor. Cells were 80% confluent in each flask and elongated epithelial cells were visible in high numbers in the EGF containing flasks in areas with low cell density at the time of protein extraction.

Cells in each group of three identical flasks were combined and extracted with 25 mM Tris-hydrochloride (pH 7.6), 0.6M KCl 1% Triton X-100, 1 mM EDTA, 1 mM EGTA, 1 mM PMSF, 10 μg/ml antipain, and 5 μg/ml pepstatin (Schermer, Galvin, and Sun, 1986). The supernatant was collected after centrifugation at 15,000 RPM for 10 minutes at 4° C. The precipitate containing insoluble proteins was further extracted and solubilized with 1% SDS in 25 mM Tris-hydrochloride (pH 7.6).

Protein determinations were performed using the BioRad (Hercules, Calif.) protein assay. Proteins (20 μg/lane soluble protein on the keratin K3 blot and 2 μg/lane insoluble protein on the enolase blot) were resolved with low range prestained SDS-PAGE standards (BioRad, Hercules, Calif.) by SDS-polyacrylamide gel electrophoresis and immunoblotted by a modification of a previously described method (Sambrook, Fritsch, and Maniatis, 1989).

Briefly, protein samples were resolved on 10% polyacrylamide gels using a Mini-Protean II Cell (BioRad) and transferred to Immobilon-P membrane (Millipore) with a Mini Trans-Blot Electrophoretic Transfer Cell (Bio-Rad). After blocking with 5% nonfat dried milk in Tris-buffered saline (TBS) and washing with 0.1% Tween 20 in TBS (TTBS), the membrane with insoluble protein lanes was incubated with AE5 mouse monoclonal antibody (Schermer, Galvin, and Sun, 1986) and the membrane with soluble protein lanes was incubated with 4G10.3 mouse monoclonal antibody to enolase (Zieske, Bukusoglu, and Yankauckas, 1992). Each antibody was diluted 100-fold in TTBS.

The membranes were washed with TTBS and incubated with TTBS containing anti-mouse IgG peroxidase linked species-specific $F(ab')^2$ fragment from sheep (Amersham). Target proteins were visualized using the ECL Western Blotting Detection System (Amersham). Identical lanes from the same gels containing soluble or insoluble proteins were stained with coomassie blue and photographed to demonstrate similar protein levels in each sample.

EXAMPLE 1

Detection of hepatocyte growth factor mRNA in corneal epithelial cells has not been previously reported, although it has been detected in vascular endothelial cells and Kupffer cells in the liver (Attisano, et al., 1992). The following experiment confirms the presence of HGF, KGF and their respective receptors in corneal endothelial and epithelial cells.

HGF, KGF, HGF Receptor, KGF Receptor and FGF Receptor-2 mRNA in Human Corneal Cells Human corneas stored for less than 96 hours in Optisol (Chiron Ophthalmics, Irvine, Calif.) were obtained from eye banks. Corneas were of transplant quality but were excluded from clinical use because of non-ocular exclusion criteria. Donors varied in age from term to 20 years of age, but all primary corneal endothelial cell cultures were derived from infant donors less than 6 months of age.

Senescent primary endothelial cell cultures were maintained without passage for 3 months until the majority of cells had the large, irregular, vacuolated, and sometimes multinucleated morphology characteristic of senescent corneal endothelial cells. Transfected endothelial cells 1, 2, and 3 were from three independent strains of cells transfected with the SV40 large T antigen coding plasmid pSV$_3$-neo. These cell strains were at passage 10, 25, and 21, respectively, with all passages after transfection being performed at a 1:2 split. Fetal calf serum and other reagents used for tissue culture were obtained from JRH Biosciences (Lanexa, Kans.). Anti-cytokeratin antibody immunofluorescence studies demonstrated that cultures of corneal epithelial cells (positive staining) prepared by these methods are pure cultures (Niederkorn, et al., 1990).

Normal human corneal epithelium was obtained for ex vivo studies by scraping the central cornea with a Paton spatula at the time of epikeratophakia or penetrating keratoplasty for an anterior stromal scar (Wilson, et al., 1992). Ex vivo corneal endothelium was obtained from the recipient button removed at the time of penetrating keratoplasty for an anterior stromal scar. Ex vivo tissues were immediately transferred into guanidinium thiocyanate (GTC) solution and used for RNA isolation (Wilson, et al., 1992). The research followed the tenets of the Declaration of Helsinki: informed consent was obtained from each patient prior to surgery after the nature and the possible consequences of the study were explained, and the research project was approved by the Investigational Review Board at the University of Texas Southwestern Medical Center (Dallas, Tex.).

Total cellular RNA and complementary DNA (cDNA) was prepared from 25 cm$^2$ flasks of near confluent cells using oligo dT primer (Wilson, et al., 1992) except that all cDNA reactions were prepared with 10 µg of total cellular RNA per 100 µl reaction. All of the RNA isolated from an ex vivo endothelial or epithelial specimen was included in a 70 µl cDNA synthesis (Wilson, et al., 1992) Mock cDNA samples were prepared using identical methods and reagents but no tissue was added to the RNA preparation.

The PCR primers that were used to amplify the cDNA sequences for beta actin, hepatocyte growth factor, hepatocyte growth factor receptor, keratinocyte growth factor, keratinocyte growth factor receptor, and FGF receptor-2 are described in Table 1. Beta actin served as an internal control for the efficiency of RNA isolation and cDNA synthesis in each sample. For the known genomic sequences, primer pairs were designed so that amplification of contaminating genomic DNA sequences would produce PCR products that were larger than PCR products amplified from cDNA (Table 1). The software program Oligos (National Biosciences, Inc., Plymouth, Minn.) was used to design PCR primers that were optimal and that would amplify at similar temperatures and magnesium concentrations. In addition, all primers and probes were compared to the Genebank and EMBL nucleic acid sequence libraries using the Intelligenetics Suite (Intelligenetics, Inc., Mountain View, Calif.) program to insure that they would not hybridize to any other known nucleic acid sequences under the conditions used. All PCR primers, except those for beta actin, were designed as part of the present invention using published nucleic acid sequences (Table 1). KGF PCR primers were synthesized 5' to 3' with a CTCCTCCTC (SEQ ID NO:1) clamp, a NotI site (GCGGCCGC) and the KGF sequence to facilitate cloning into vectors that require restriction digestion. Restriction sites were eliminated and the clamp was reduced to CTC on other primers with use of the TA Cloning System (Invitrogen, San Diego, Calif.) that does not require restriction digestion of the amplified product for cloning. All oligonucleotides were synthesized by Oligos etc. (Guilford, Conn.).

TABLE 1

Expected sizes of PCR amplification products with each primer pair.

| MODULATOR | SIZE | REFERENCES | UPSTREAM PRIMER | DOWNSTREAM PRIMER | PROBE |
|---|---|---|---|---|---|
| Beta actin | 350/790 | Mivechi et al. Ng S-Y et al. | 1628–1650 [GAAGTCCAGGGCGACGTAGCAC] (SEQ ID NO:2) | IC 2379–2400 [GAAGTCCAGGGCGACGTAGCACA] (SEQ ID NO:2) | None |
| HGF | 384/* | Nakamura et al. Miyazawa et al. | 976–999 [AGTACTGTGCAATTAAAACATGCG] (SEQ ID NO:3) | IC 1333–1353 [TTGTTTGCGATAAGTTGCCCA] (SEQ ID NO:9) | IC1015–1044 [CAGTTGTTTCCATATGGAACATCAGTATCAT] (SEQ ID NO:14) |
| HGF receptor | 342/unk | Park et al. | 3993–4013 [TGGTCCTTTGGCGTCGTCCTC] (SEQ ID NO:4) | IC 4308–4328 [CTCATCATCAGCGTTATCTTC] (SEQ ID NO:10) | IC 4134–4164 [CTTTAGCGGTGCCAGCATTTTAGCATTACTT] (SEQ ID NO:15) |
| KGF | 669/un | Finch et al. | 1488–1509 [GCCACACTAACTAACTATGGAAAATG] (SEQ ID NO:5) | IC 2128–2150 [TTCCAGGATTTGCTCGGCCCAAGT] (SEQ ID NO:11) | IC 1910–1929 [CCATAGGAAAAAAGCATGATTATTTGTGGG] (SEQ ID NO:16) |
| KGF receptor | 178/1200 | Miki et al. | 3–23† [GGATCAAGCACGTGGAAAAGA] (SEQ ID NO:6) | IC 83–103¶ [GCCCTATATAATTCGAGACCT] (SEQ ID NO:12) | IC 30–60¶ [GCCTCGGTCACATTGAACAGAGCCAGCACT] (SEQ ID NO:17) |
| FGF recept-2 | 205/2400 | Miki et al. | 3–23† [GGATCAAGCACGTGGAAAAGA] (SEQ ID NO:7) | IC 110–130§ [ACCATGCAGAGTGAAAGGATA] (SEQ ID NO:13) | IC 30–59§ [GTTACATTCCGAATATAGAGAACCTCAATC] (SEQ ID NO:18) |

Size indicates the expected size of the amplified sequences from cDNA or genomic DNA, including 5' clamps included on primers for growth factors, cytokines, and receptors.
Unknown indicates that the genomic sequence has not been reported. The references are those for the cDNA/genomic sequences.
IC indicates that the primer or probe was the inverse complement of the specified nucleotides from the indicated reference. All primers and probes were designed by the authors except those for beta actin that were obtained from the listed reference. All sequences are the actual primer and probe sequences from 5' to 3', but CTC clamps that were included at the 5' end of primers are not shown. The size of the beta actin fragment does not correspond to the nucleotide numbers since the referenced sequence is for genomic DNA and includes an intron that is excised during RNA processing.
†, ¶ and § indicate exons U, K, and B, respectively, of the provided reference. Note that KGF receptor and FGF receptor-2 sequences are amplified using the same upstream primer.
*Complete HGF genomic organization has not been reported, but the upstream primer is in exon 7 and the downstream primer is in exon 10 and, therefore, genomic amplification from these primers would be much larger than 384 base pairs.

PCR amplification of each sequence was performed with 5 μl of cDNA sample from cell cultures or 10 μl of cDNA from ex vivo samples in a total volume of 100 μl using 2 units of Taq polymerase (Promega, Madison, Wis.) and 1.5 mM magnesium (Wilson, et al., 1992). All of the test samples were amplified simultaneously with a particular primer pair and a master mix containing all of the components in the PCR reaction, except the target cDNA or water negative control, was used to prepare the individual reactions. All PCR reactions were prepared using the hot start method (D'Aquila, et al., 1991) in which the target and PCR master mix solution were brought to 80° C. prior to mixing and were maintained at that temperature for several minutes before beginning the PCR cycle. Control reactions without template were included with each amplification for each pair of primers. Programmable temperature cycling (Ericomp, Inc., La Jolla, Calif.) was performed with the following cycle profile: Denaturation 4 minutes at 94° C., followed by 40 cycles of annealing 3 seconds at 55° C., extension 1 minute at 72° C., and denaturation 30 seconds at 94° C. Horizontal 1.5% agarose (US Biochemical Corp, Cleveland, Ohio) gel electrophoresis was performed by a previously described technique (Wilson, et al., 1992) Twenty seven μl of each PCR product was evaluated in a slot on a 120 ml gel. One hundred base pair DNA ladder or φX174/Hae III fragments (Bethesda Research Laboratories, Gaithersburg, Md.) were used as molecular size standards. Unless otherwise specified, all reagents were obtained from Sigma (St Louis, Mo.).

The hot blot method was used to demonstrate that each of the amplified sequences was specific. The probes used to detect the amplified sequences (Table 1) were designed to be complementary to an internal sequence in the amplified region that did not overlap with the PCR primer sequences. Size markers were included on each hot blot gel and were photographed with a ruler aligned with the markers to allow calculation of the sizes of the products detected on the auto radiograms.

Figure 1B:
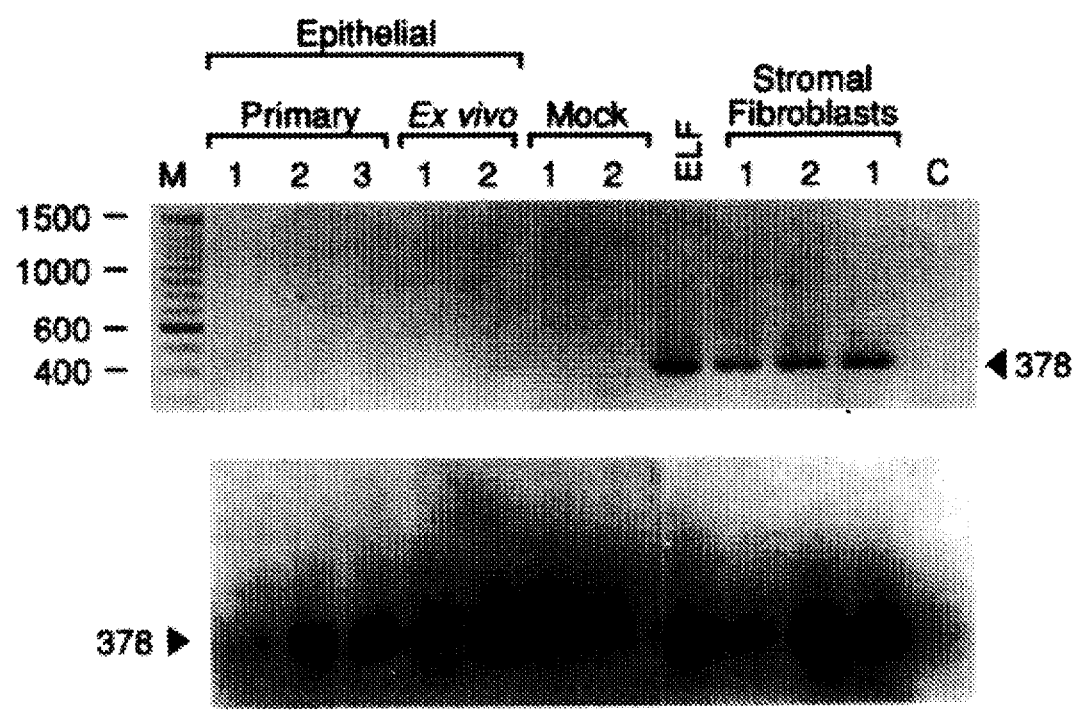
FIG. 1B. Primary epithelial cells, ex vivo corneal epithelium, embryonic lung fibroblasts (ELF), primary stromal fibro- blasts (1), and first passage stromal fibroblasts (2). Mocks were amplified with samples that had undergone RNA preparation and cDNA synthesis without added tissue. Lane C is a simultaneous control amplification with water. Lanes marked with M indicate the φX174 Hae III markers. Lengths of selected markers in base pairs are provided to the left. The arrowhead indicates the product of the expected length of 378 base pairs. Hot blots of the same samples (lower panels) demonstrate the specificity of the 378 base pair PCR product.

FIG. 1 shows that hepatocyte growth factor mRNA PCR amplifications were strongest in stromal fibroblasts and embryonic lung fibroblasts. Hepatocyte growth factor was also readily detectable in proliferative primary, senescent primary, and transfected corneal endothelial cells. Hepatocyte growth factor mRNA was present in corneal epithelial cells in much smaller amounts compared to stromal fibroblasts and corneal endothelial cells based on visual inspection of the ethidium bromide stained agarose gels in FIG. 1. Hepatocyte growth factor mRNA was present in variable amounts in all three major cell types of the cornea. There is a marked difference in the amplified signal in the stromal fibroblast and endothelial cell samples compared to the corneal epithelial samples. These data demonstrated that human corneal epithelial cells and corneal endothelial cells produced messenger RNA coding for hepatocyte growth factor.

Figure 2A:
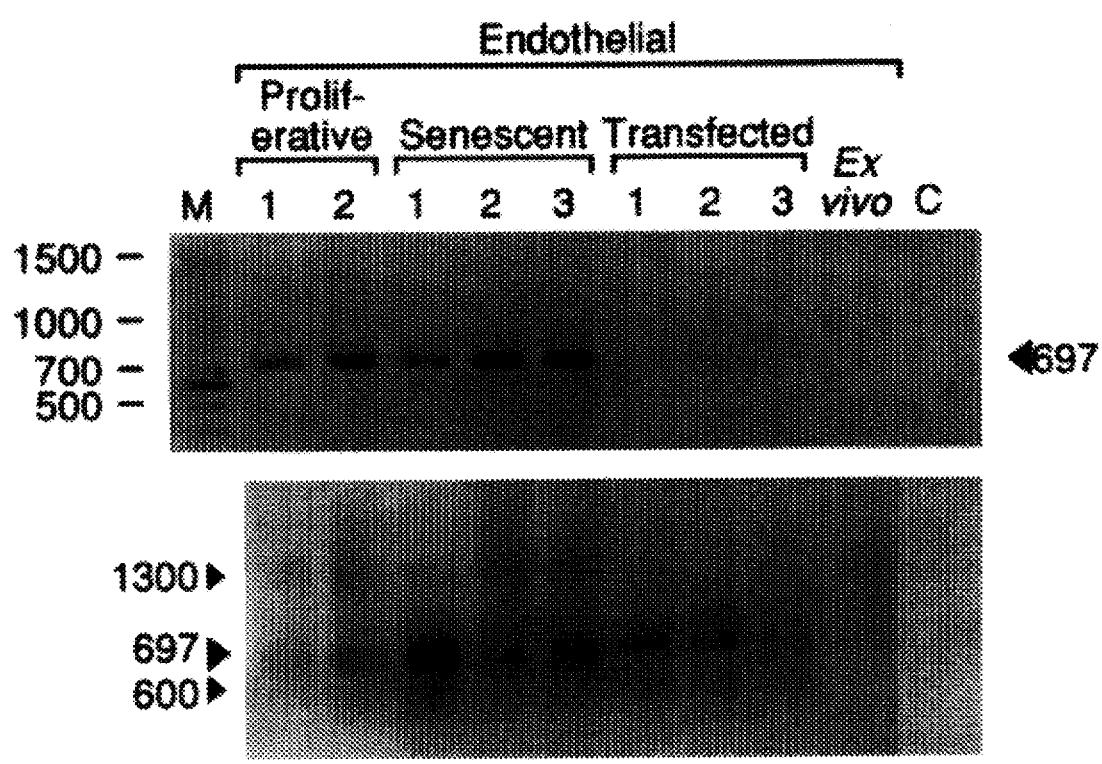
FIG. 2A. Keratinocyte growth factor PCR-amplified products that were amplified using the hot start method from the cDNA samples generated from human cells. Shown are primary proliferative endothelial cells, primary senescent endothelial cells, SV40 large T antigen-transfected endothelial cells and ex vivo endothelium.
Figure 2B:
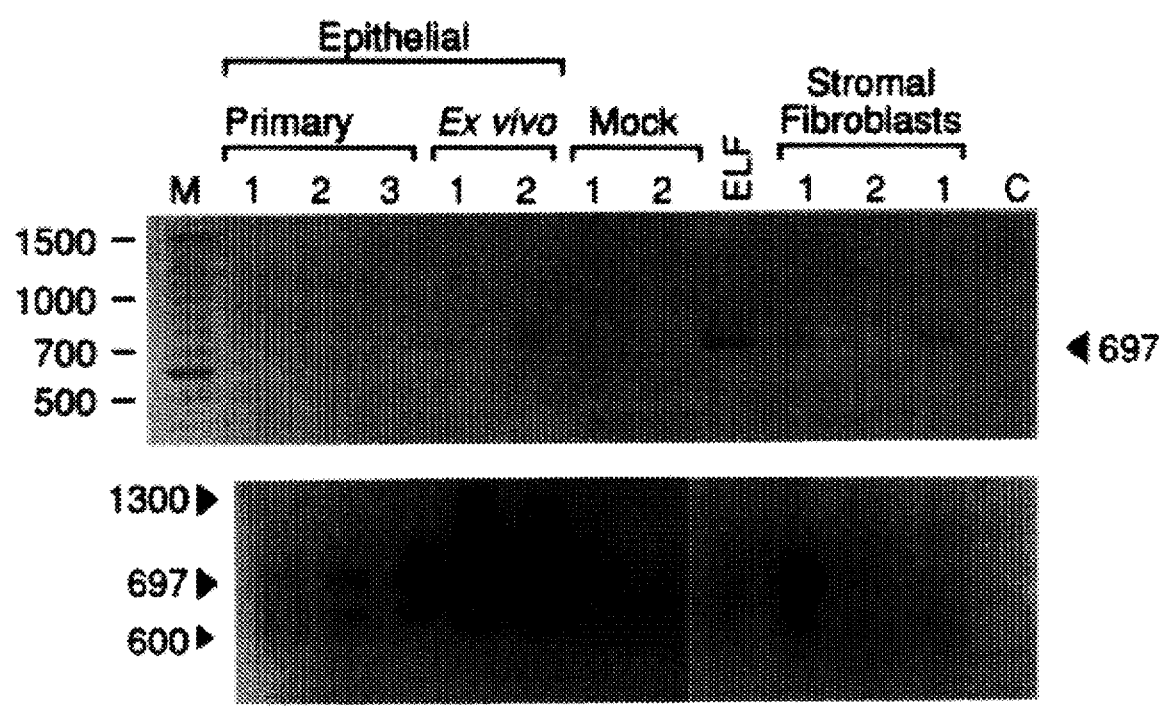
FIG. 2B. Primary epithelial cells, ex vivo corneal epithelium, embryonic lung fibroblasts (ELF), primary stromal fibroblasts (1), and first passage stromal fibroblasts (2). Mocks were amplified with samples that had undergone RNA preparation and cDNA synthesis without added tissue. Lane C is a simultaneous control amplification with water. Lanes marked with M indicate the 100 base pair size markers. Lengths of selected markers in base pairs are provided to the left. The arrowhead indicates the product of the expected size of the 697 base pairs on both the PCR products (upper panels) and hot blot (lower panels).

FIG. 2 shows that the 697 base pair KGF specific amplification product was detectable in each of the cell types evaluated. This amplification product was prominent in the proliferative and senescent corneal endothelial cells and stromal fibroblasts, but was also detectable in transfected corneal endothelial cells and primary corneal epithelial cells. The hot blots in FIG. 4 demonstrated that the 697 base pair amplification product was specific for KGF and that the product was detectable in corneal epithelial cells. In addition, other KGF specific amplification products at approximately 600 and 1300 base pairs were detected in some of the cells. The latter products could not be detected on the ethidium bromide stained gels. The approximately 600 base pair amplification product was detectable in each of the cell types of the cornea, but appeared to be slightly larger in the transfected endothelial cell. The 1300 base pair amplification product was detectable in only one of the epithelial samples, ex vivo sample 1 (FIG. 2B). While Langerhan's cells and possibly other cell types present in the ex vivo corneal epithelial tissue may have contributed to the KGF signal, it is likely that the different sized products were amplifications from different keratinocyte growth factor-specific mRNA transcripts in all three major cell types of the cornea, albeit at lower levels in the corneal epithelial cells.

Figure 3A:
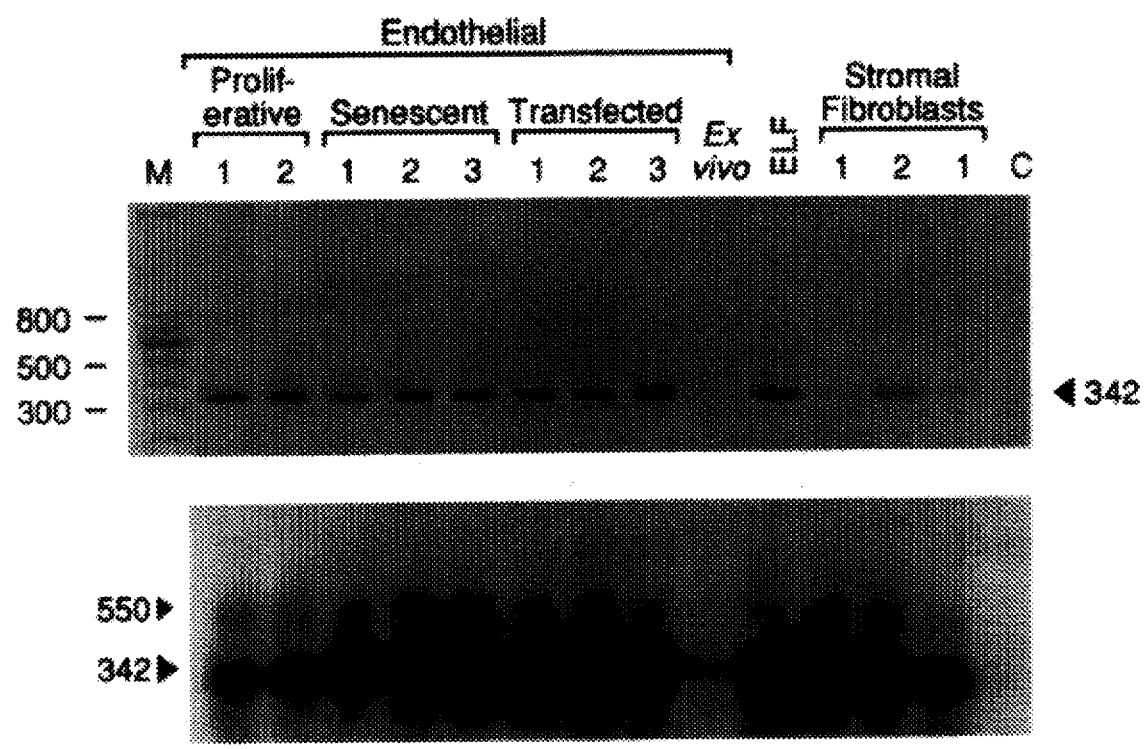
FIG. 3A. Hepatocyte growth factor receptor PCR products amplified in the same experiment using the hot start method from the cDNA samples generated from human cells. Shown are primary proliferative endothelial cells, primary senescent endothelial cells, SV40 large T antigen-transfected endothelial cells, ex vivo endothelium (ex), embryonic lung fibroblasts (ELF), primary stromal fibroblasts (1) and first passage stromal fibroblasts (2).
Figure 3B:
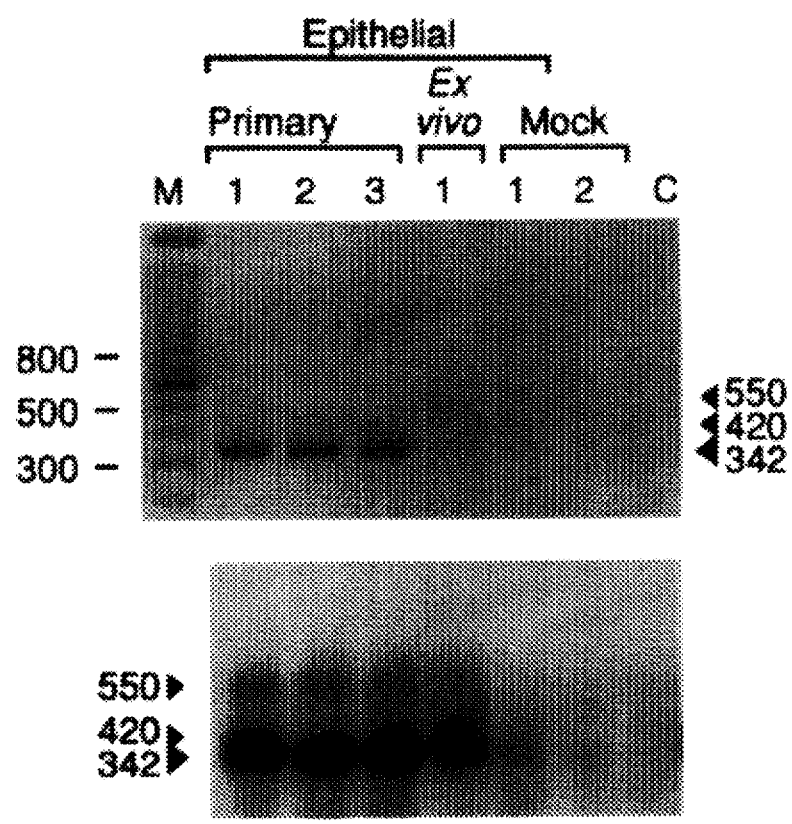
FIG. 3B. Primary epithelial cells, and ex vivo corneal epithelium. Mocks were amplified with samples that had undergone RNA preparation and cDNA synthesis without added tissue. Lane C is a simultaneous control amplification with water. Lanes marked with M indicate the 100 base pair size markers. Lengths of selected markers in base pairs are provided to the left. The arrow indicates the PCR products (upper panel) and the hot blot bands (lower panels) of the expected size of 342 base pairs.

FIG. 3 shows that amplification products of the expected size for the hepatocyte growth factor receptor (342 base pairs) were detectable in each of the cell types evaluated. The hot blots in FIG. 3 show that the amplification product of the expected size was specific for hepatocyte growth factor receptor. In addition, a specific alternative PCR product approximately 550 base pairs in size was detected in each cell type. An additional band at approximately 420 base pairs was present in the ex vivo epithelium sample on the ethidium bromide stained gel and the hot blot (FIG. 3B). This 420 base pair product may represent a PCR amplification product that was derived from an alternative hepatocyte growth factor receptor mRNA. The major amplification product on the ethidium bromide stained agarose gel was 342 base pairs in size. Hot blots of the same samples demonstrate the specificity of the 342 base pair PCR product and revealed an amplified product identified by the hepatocyte growth factor receptor probe in some samples at 550 base pairs. An amplified product in ex vivo epithelial sample 1 at approximately 420 base pairs was also detected on the hot blot. The data represented in FIG. 3 demonstrate that human corneal epithelial cells and corneal endothelial cells produce messenger RNA coding for hepatocyte growth factor receptor.

Figure 4A:
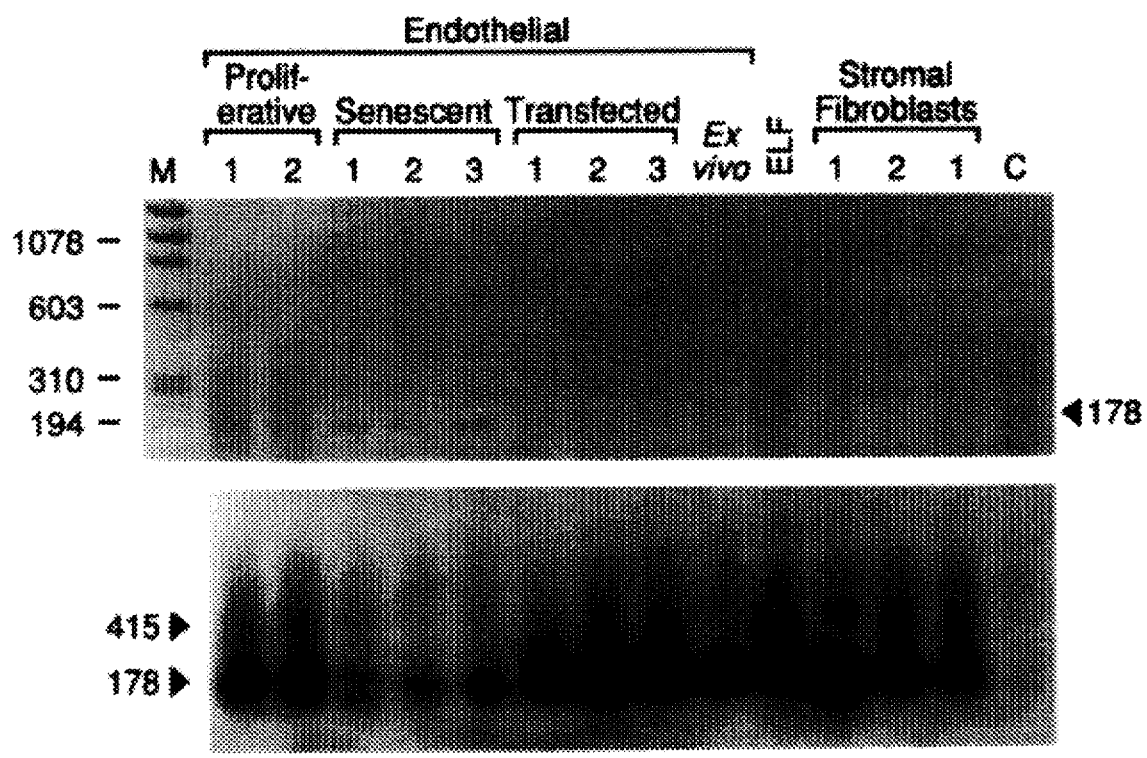
FIG. 4A. Keratinocyte growth factor receptor PCR products amplified in the same experiment using the hot start method from the cDNA samples generated from human cells. Shown are primary proliferative endothelial cells, primary senescent endothelial cells, SV40 large T antigen-transfected endothelial cells, ex vivo endothelium (ex), embryonic lung fibro- blasts (ELF), primary stromal fibroblasts (1) and first passage stromal fibroblasts (2).
Figure 4B:
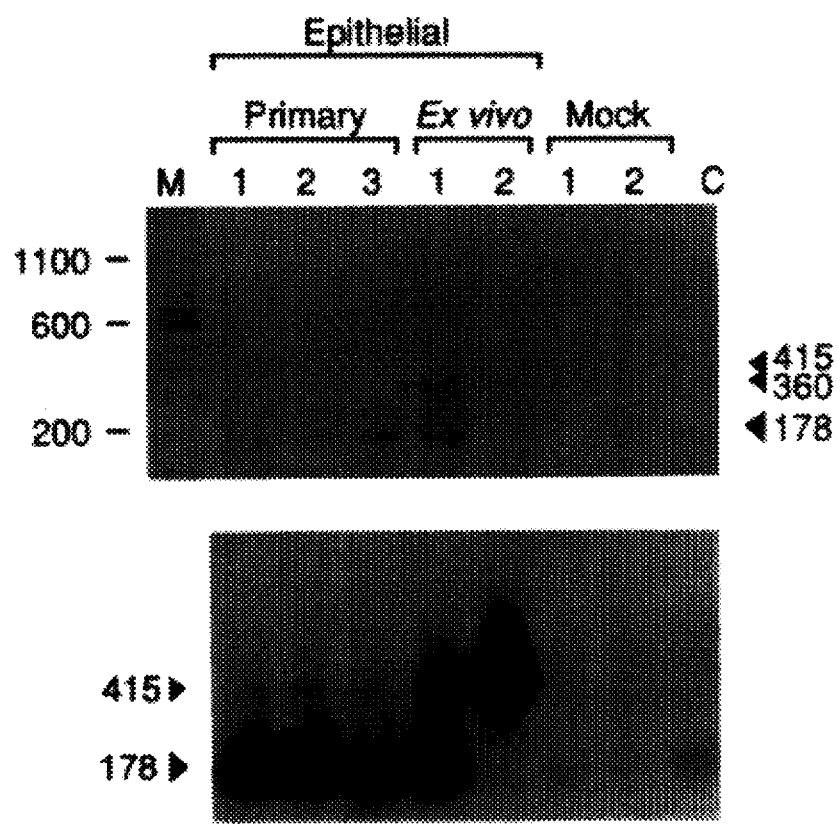
FIG. 4B. Primary epithelial cells and ex vivo corneal epithelium. Mocks were amplified with samples that had undergone RNA preparation and cDNA synthesis without added tissue. Lane C is a simultaneous control amplification with water. Lanes marked with ∅X and M indicate φX174 Hae III and 100 base pair size markers, respectively. Lengths of selected markers in base pairs are provided to the left. The arrow indicates the PCR products (upper panels) and hot blot bands (lower panels) of the expected size of 178 base pairs.

Keratinocyte growth factor receptor and FGF receptor-2 are derived by alternative mRNA splicing from the same gene (bek), with keratinocyte growth factor receptor having a high affinity for keratinocyte growth factor and acidic FGF and FGF receptor-2 having a high affinity for basic and acidic FGF (Miki, et al., 1992). Specific amplification products of the expected size for the keratinocyte growth factor receptor (178 base pairs) were also detectable in each of the cell types evaluated (FIG. 4). The corresponding band in ex vivo epithelial cell sample 2 was shifted to a slightly larger size relative to the adjacent bands (FIG. 6B). Also, in the ex vivo epithelium sample, two additional bands were noted at approximately 415 and 360 base pairs. Hot blots of the same samples demonstrated the specificity of the 178 base pair PCR product and revealed the 415 base pair amplified product in several samples. The latter band was prominent in ex vivo epithelium sample 2. The shifted lower band at approximately 200 base pairs and the 360 base pair band in ex vivo epithelium sample 2 (FIG. 4) were not identified on the hot blot. The 415 base pair PCR products were not large enough to represent amplifications from genomic DNA (Table 1) and, therefore, most likely represent amplifications from precursor RNAs or alternatively-spliced mRNA transcripts.

EXAMPLE 2

The work described in the following example on corneal epithelial and corneal endothelial cells shows that hepatocyte growth factor and keratinocyte growth factor can be used to regulate corneal epithelial and endothelial wound healing or to improve the viability of corneal endothelial cells during corneal preservation.

Effects of KGF and HGF on Corneal Epithelial and Endothelial Cell Proliferation

All experiments on the effects of exogenous growth factors on proliferation were performed with first passage corneal epithelial and endothelial cells. Proliferation experiments were performed with Costar (Cambridge, Mass.) 12-well plates. Plates used for epithelial cell experiments were precoated with poly-D-lysine (Sigma, St Louis, Mo.) at 0.1 mg/ml in sterile water, washed twice with sterile water, coated with fibronectin (Sigma) at 50 µg/ml in HBSS, and washed with sterile medium (Marchese, et al., 1990). Plates used for stromal fibroblasts and endothelial cells were not precoated. Epithelial cell proliferation experiments were performed in Keratinocyte Defined Medium (KDM, modified MCDB 153, 5 µg/ml insulin, 0.5 µg/ml hydrocortisone, and 0.15 mM $Ca^{2+}$, and 0.1 ng/ml human epidermal growth factor (Clonetics, San Diego, Calif.).

Epithelial cells were plated for the first two days in KDM with epidermal growth factor (since cells initially plated in KDM without epidermal growth factor did not adhere well). Prior to the addition of test growth factors, epithelial cells were washed twice with KDM without epidermal growth factor and 1 ml of KDM without epidermal growth factor was added per well. Stromal fibroblast proliferation experiments were performed in Fibroblast Basal Medium (FBM, Modified MCDB 202 with 5 mg/ml insulin, Clonetics).

Corneal endothelial cell proliferation experiments were performed in medium with 0.5% fetal bovine serum as the only serum source. All growth factors were obtained commercially (human hepatocyte growth factor, #904792, Collaborative Biomedical Products, Bedford, Mass.; human keratinocyte growth factor, H-1086, Bachem, Philadelphia, Pa.; human epidermal growth factor, 920126, Collaborative Biomedical Products; human basic FGF, CC-4065, Clonetics, San Diego, Calif.). Stock growth factors were aliquoted into siliconized microtubes and stored at −80° C. so that they were thawed only one additional time prior to use.

Epithelial, stromal fibroblast, and endothelial cells were plated at 10,000 cells per well in all experiments. For each experiment, cells were plated in 1.0 ml of the appropriate medium per well and incubated for 2 days at 37° C. Cells were washed with the appropriate medium and 1.0 ml of fresh medium was added. Growth factors were then added to each well. Growth factors were diluted at the time of addition in sterile PBS with 0.2% gelatin so that 5 µl of additional volume was added to each well to give the final concentration. In each growth factor experiment, each concentration of growth factor(s) was tested in 6 wells. Twelve control wells were included to which 5 µl of PBS with 0.2% gelatin were added. Hepatocyte growth factor, keratinocyte growth factor, and epidermal growth factor were tested at 50, 25, 10, 5, 2.5, and 1 ng/ml. As a positive control, basic FGF was tested at 25 ng/ml in the stromal fibroblast experiments. In the combined growth factor experiment for corneal epithelial cells, each growth factor was tested at 10 ng/ml, individually or in combination, in each well. Cells were incubated an additional 5 days at 37° C. after the addition of growth factors. Each well was then washed twice with 1.0 ml of PBS, trypsinized to complete dissociation with 0.5 ml of 0.25% trypsin (approximately 10 minutes), and the cells in each well transferred quantitatively to a Coulter vial with Coulter fluid to give a final volume of 10 ml per well. The total number of cells for each well was determined from the average of 3 measurements, minus the background, determined with a Coulter counter (Model Zf, Hialeah, Fla.). Errors were expressed as the standard error of the mean.

Statistical comparisons were performed with the Newman-Keuls nonparametric multiple comparison test. A Z value less than 0.05 was considered statistically significant.

Exogenous hepatocyte growth factor and keratinocyte growth factor significantly stimulated the proliferation of first passage corneal epithelial and endothelial cells from young human donors in a dose response manner (FIGS. 5, 6, 7 and 8) up to about 50 ng/ml. EGF showed stimulation up to about 25 ng/ml. Generally, HGF and KGF stimulated proliferation in both cell types at lower concentrations than did EGF. The stimulatory effect of HGF, KGF and EGF was not present at higher concentrations. Combinations of HGF, KGF and EGF did not increase corneal epithelial cell proliferation. When the three growth factors were combined at concentrations of 10 ng/ml each, however, there was no longer a significant effect on proliferation. Corneal epithelial cell proliferation was increased by HGF and KGF in defined serum-free medium with 0.15 mM $Ca^{2+}$.

Hepatocyte growth factor, however, stimulated corneal cell proliferation at 1.8 mM $Ca^{2+}$, but suppressed proliferation at 0.1 mM $Ca^{2+}$ (data not shown).

Figure 5:
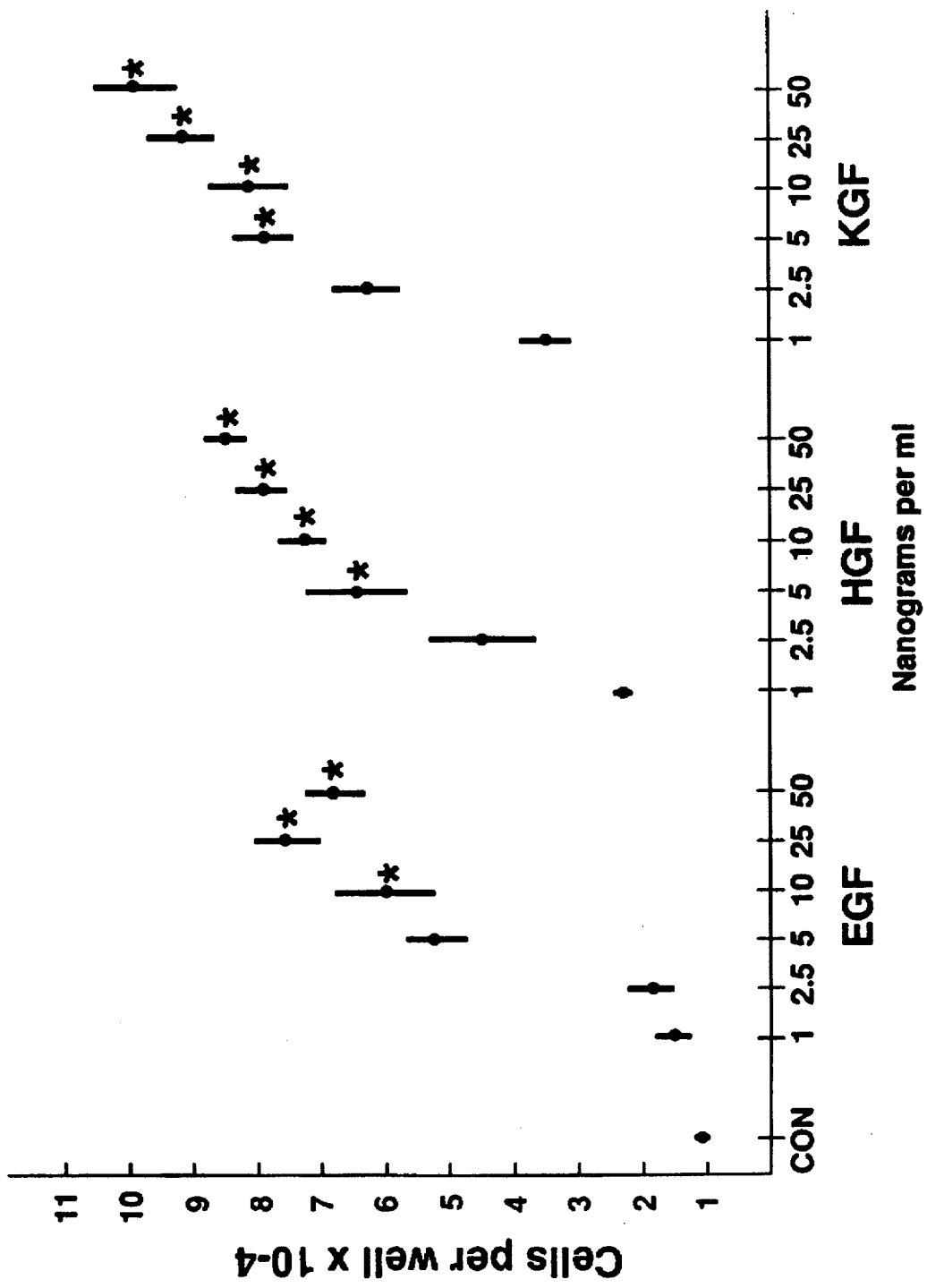
FIG. 5. Mitogenic effects of epidermal growth factor, hepatocyte growth factor, and keratinocyte growth factor on the first passage human corneal epithelial cells (experiment 1). Data are presented as the mean ± the standard error of the mean for the 12 control wells and the 6 wells for each growth factor concentration in each experiment. Asterisks (*) indicate that the effect was statistically significant compared to the control group.
Figure 6:
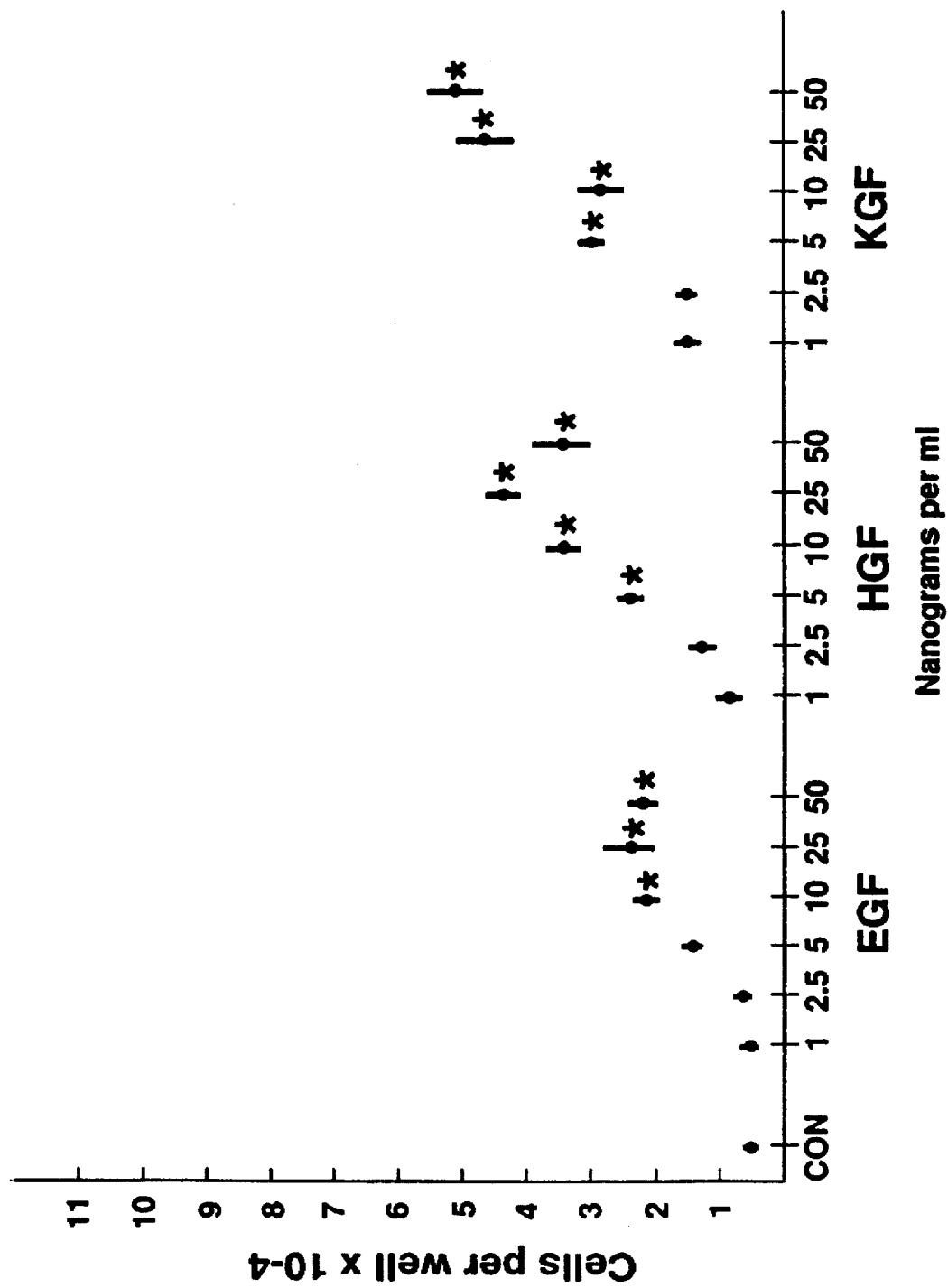
FIG. 6. Mitogenic effects of epidermal growth factor, hepatocyte growth factor, and keratinocyte growth factor on the first passage human corneal epithelial cells (experiment 2). Data are presented as the mean ± the standard error of the mean for the 12 control wells and the 6 wells for each growth factor concentration in each experiment. Asterisks (*) indicate that the effect was statistically significant compared to the control group.
Figure 7:
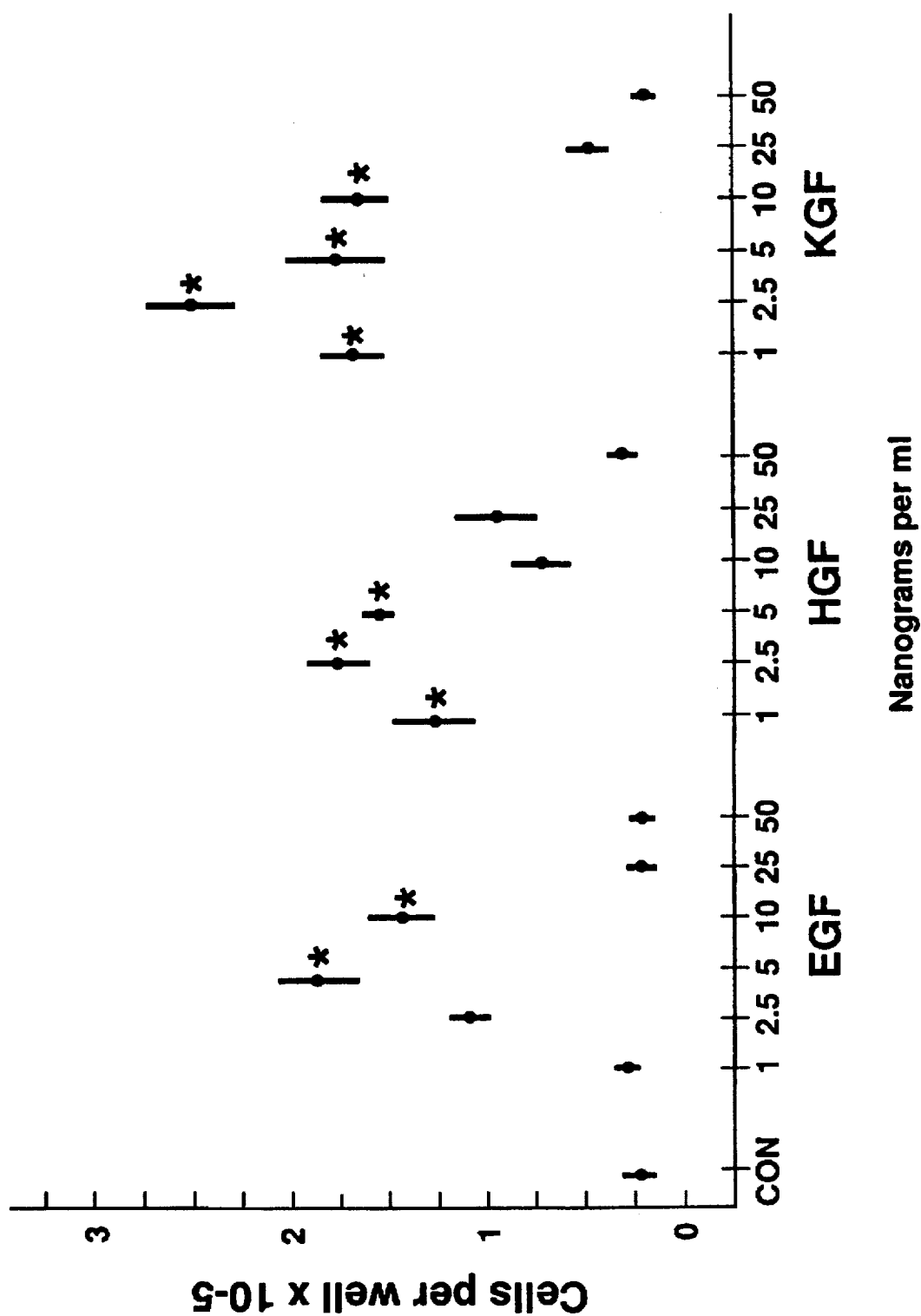
FIG. 7. Mitogenic effects of epidermal growth factor, hepatocyte growth factor, and keratinocyte growth factor on the first passage human corneal endothelial cells (experiment 1). Data are presented as the mean ± the standard error of the mean for the 12 control wells and the 6 wells for each growth factor concentration in each experiment. Asterisks (*) indicate that the effect was statistically significant compared to the control group.
Figure 8:
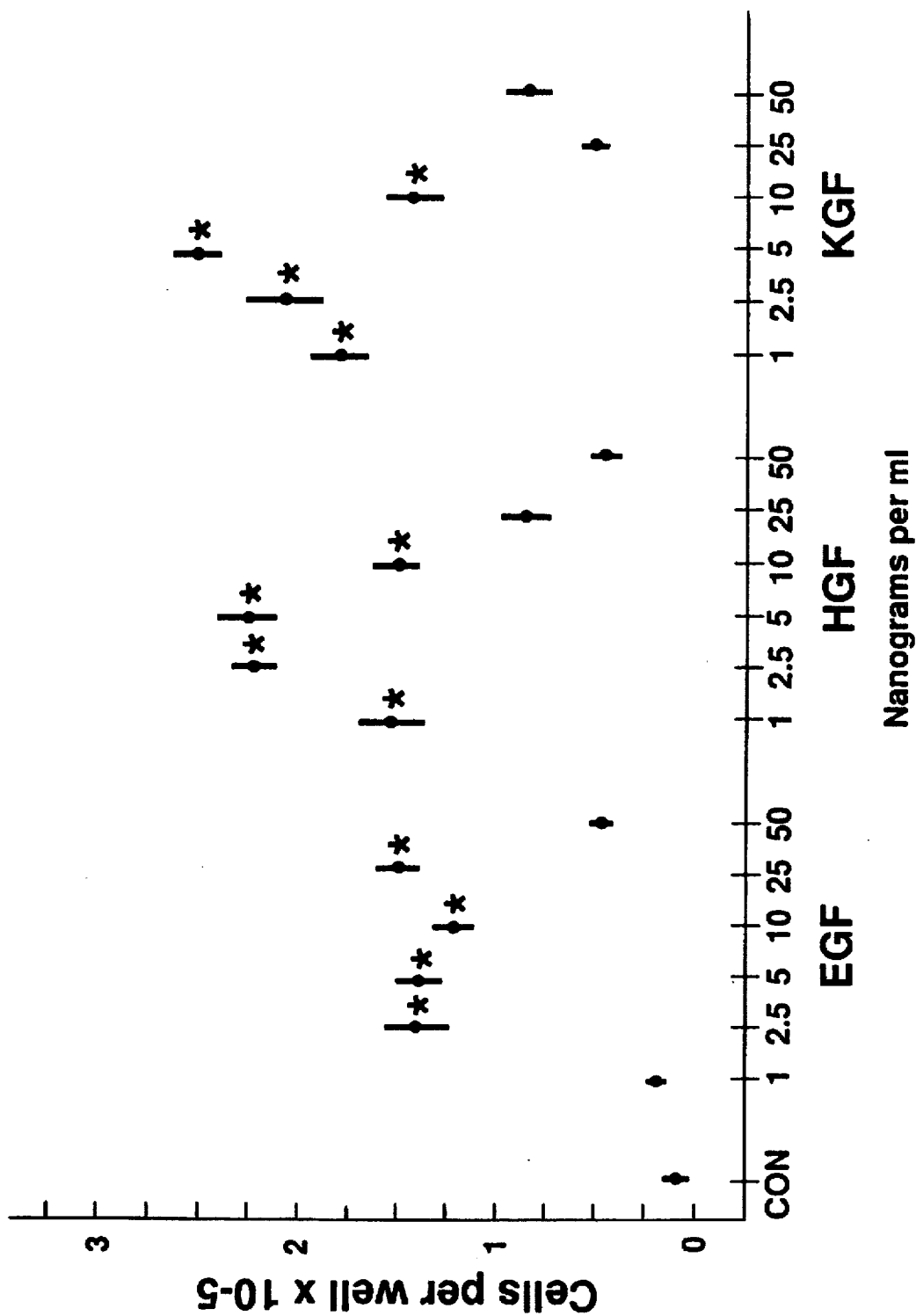
FIG. 8. Mitogenic effects of epidermal growth factor, hepatocyte growth factor, and keratinocyte growth factor on the first passage human corneal endothelial cells (experiment 2). Data are presented as the mean ± the standard error of the mean for the 12 control wells and the 6 wells for each growth factor concentration in each experiment. Asterisks (*) indicate that the effect was statistically significant compared to the control group.

Corneal epithelial cell proliferation was stimulated by either HGF or KGF at concentrations up to about 50 ng/ml. EGF stimulation dropped above a concentration of about 25 ng/ml. At 1 ng/ml, EGF had little or no effect on corneal epithelial stimulation, but there was noticeable stimulation by either HGF or KGF at this concentration. At 2.5 ng/ml, both KGF and HGF showed significantly greater stimulatory effects than EGF (see FIG. 5 and FIG. 6). Maximal corneal epithelial cell stimulation by HGF or KGF was in the range of about 50 ng/ml, although maximal stimulation for KGF may have been somewhat higher as indicated in FIG. 5. Doses higher than 50 ng/ml were not tested.

Corneal endothelial proliferation was significantly stimulated by HGF or KGF at 1 ng/ml. Virtually no stimulation was observed with EGF at this concentration (see FIG. 7 and FIG. 8). Maximal stimulation for either HGF or KGF was at a concentration of about 2.5 ng/ml.

Increased proliferation of corneal epithelial and endothelial cells in response to exogenous hepatocyte growth factor and keratinocyte growth factor indicates a function in controlling proliferation in these cell types. HGF and KGF also are useful for storing corneas in preservation medium prior to corneal transplant. These factors appear to have a trophic effect on corneal cell stimulation, indicating that viability of corneal epithelial cells and endothelial cells will be improved.

EXAMPLE 3

The following results demonstrate that EGF, heparin binding EGF, TGF apha, or double-chain HGF (DC-HGF stimulates proliferation and motility and inhibits expression of keratin K3.

MITOSIS: Initial increases in cell numbers were visually noted in flasks with individual growth factors or combinations of EGF, KGF, and SCDC-HGF. Approximately 6–8 days after initiating the experiments, elongated cells with prominent extensions were noted in flasks containing EGF. Human corneal epithelial cells were observed after 14 days of exposure to vehicle, or individual growth factors [EGF, SCDC-HGF, and KGF. Large numbers of elongated cells that appeared to have extensions appeared after approximately 6 days in cultures containing EGF. A few elongated cells were at times noted in cultures without EGF, but they were very rare. Heparin-binding EGF and double-chain HGF produced effects similar to EGF.

Human corneal epithelial cells were also observed after 14 days of exposure to combinations of growth factors EGF and SCDC-HGF, EGF and KGF, SCDC-HGF and KGF, and EGF, SCDC-HGF, and KGF. Large numbers of the elongated cells appeared after approximately 6 days in cultures containing EGF, even when other growth factors were present. These elongated cells were noted in all cultures incubated with EGF, regardless of whether EGF was present alone or in combination with SCDC-HGF and/or KGF. Few, if any, elongated cells with extensions were noted with SCDC-HGF, KGF, or combined SCDC-HGF and KGF. These elongated cells persisted in wells containing EGF and a progressive decline in the total number of cells was noted up to the time of cell counting at two to three weeks.

Figure 9:
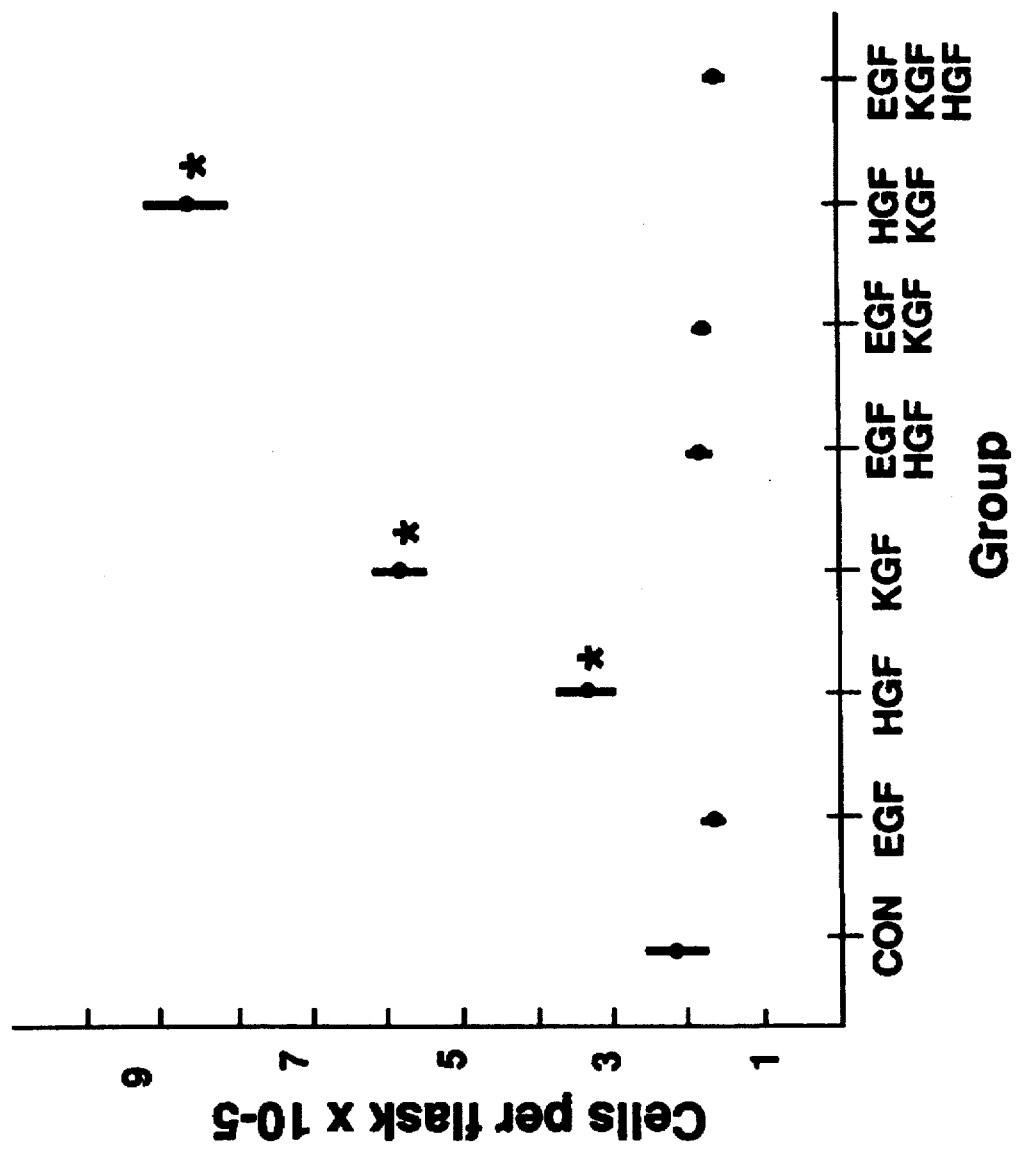
FIG. 9. Cells per T-25 flask after a 3 week exposure to growth factors. There was a statistically significant (*) increase in the number of cells in cultures containing SCDC-HGF, KGF, or SCDC-HGF and KGF. There was an increase in the number of cells with the combination of SCDC-HGF and KGF, but the difference was not statistically higher than with either growth factor alone. The total cells in all cultures containing EGF were less than that in the control flasks, but the differences were not statistically significant. Values are the mean and standard error for three replicate flasks. Results with heparin-binding EGF and double-chain HGF were similar to those with EGF (not shown).
Figure 10A:
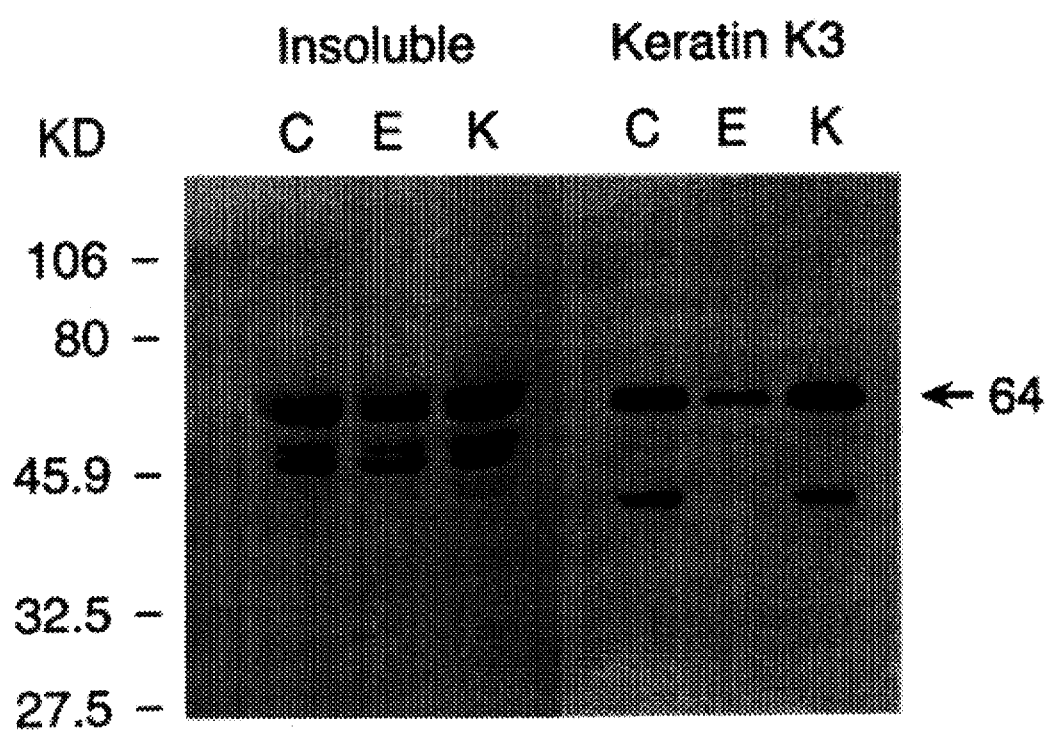
FIG. 10A. Western blotting for keratin K3 (A) protein expression in human corneal epithelial cells cultured for 7 days. Blotting was performed with insoluble fraction proteins for keratin K3 and soluble fraction proteins for enolase. The coomassie blue stained gels run in parallel with the immunoblotted gels are shown to the left of each blot and demonstrate that total protein loading was similar for the control (C), EGF-treated (E), and KGF-treated (K) cells on each blot. Prestained size markers were included on the coomassie blue stained gels and sizes in KDa are provided to the left. The keratin K3 band at 64 KDa was significantly decreased in cells maintained in EGF compared to control cells or cells maintained in KGF. Lower molecular weight bands did not react when AE5 was omitted and appear to be degradation products of keratin K3.
Figure 10B:
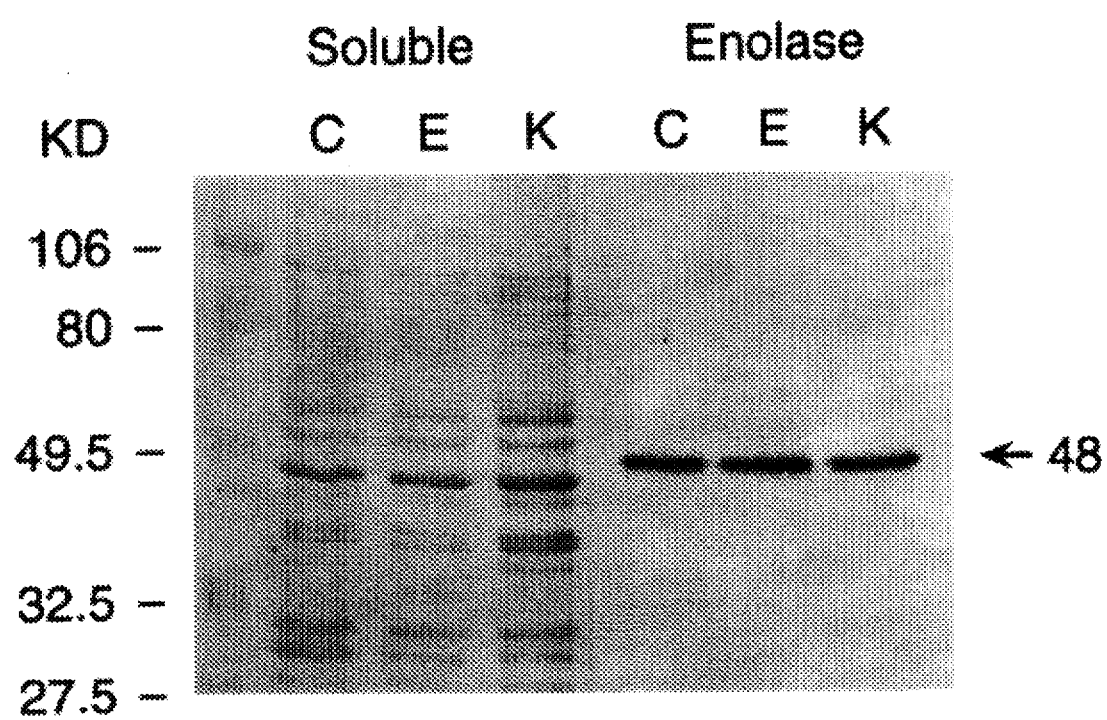
FIG. 10B. Conditions were the same as in FIG. 10A. No difference was noted in enolase (48 KDa) expression in the soluble fraction proteins between control, EGF-maintained, and KGF-maintained cells. Similar results were obtained with cultures maintained for 17 days.

After two to three weeks of incubation with the growth factors, the total number of cells was significantly increased in wells containing SCDC-HGF, KGF, or SCDC-HGF/KGF compared with the control (FIG. 9), although the increase with SCDC-HGF just reached statistical significance. There was an increase in the number of cells with the combination of SCDC-HGF and KGF, compared to either growth factor alone, but the difference was not statistically significant. The total number of cells was decreased compared to the control in all wells containing EGF, either alone or in combination with SCDC-HGF, KGF, or SCDC-HGF/KGF. However, the decrease compared to the controls did not reach statistical significance.

Individual growth factors were tested in four experiments and identical morphology was noted with EGF in each trial. In one trial, EGF that was obtained from 3 different commercial suppliers was tested and similar morphologic and proliferative results were noted with the growth factor obtained from each source at approximately 6 to 9 days after beginning the culture in serum-free KDM with EGF. These morphologic changes were not noted when human corneal epithelial cells were grown in medium containing serum.

The effect of TGF alpha was also evaluated in one of the experiments. The effect of TGF alpha on the morphology and proliferation of human corneal epithelial cells in serum-free defined medium was identical to that noted with EGF.

The effect of HB-EGF, SC-HGF, or DC-HGF on proliferation were tested. HB-EGF and DC-HGF effects were virtually the same as EGF, with initial increases in cell numbers followed by the appearance of elongated cells and a decline in cell number. Pure SC-HGF was identical to the control and did not stimulate proliferation or a change in morphology.

MOTILITY: The elongation of cells seeded at low density in cultures exposed to EGF and DC-HGF suggested that EGF increased motility. The central chamber experiment was designed to detect motility since directional movement away from the initial central cell mass could be detected, whereas random movement in the previous experiments would not be obvious. The cells plated within the cloning cylinder produced a confluent, multilayered, central mass of cells with a relatively sharp edge. The edge of the confluent, central patch of human corneal epithelial (HCE) cells after removal of the cloning cylinder was relatively uniform in all cultures. After two weeks of exposure to vehicle there was little change in the cells at the edge of the cell mass. In contrast, in wells containing EGF (EGF) there were large numbers of elongated cells, many of which were separated from the expanding cell mass. Cells tended to be larger in wells with EGF, compared to control cells. The edge of the cell mass in wells containing KGF (KGF) became irregular, with groups of cells extending beyond the origin of the cell mass. In addition, throughout the cell mass individual cells tended to have smaller diameters. In wells containing single-chain HGF (HGF) there was no tendency for cells to extend beyond the origin. Heparin binding EGF and double-chain HGF produced results that were similar to EGF. Little difference was noted between control and growth factor containing wells until approximately 6 days. At this point elongated cells identical to those noted in the proliferation experiments were obvious at the edge of the central island of cells in wells containing EGF and the perimeter of the cell mass progressively expanded until the experiments were terminated at 14–18 days of culture (Table 2).

TABLE 2

EFFECT OF GROWTH FACTORS ON MOTILITY OF HUMAN CORNEAL EPITHELIAL CELLS

| GROWTH FACTOR | CENTRAL ISLAND AREA RATIO TO CONTROL |
|---|---|
| EGF | 2.4 ± 0.4** |
| HB-EGF | 1.8 ± 0.4** |
| SC-HGF | 1.0 ± 0.0 |
| DC-HGF | 2.2 ± 0.4** |
| KGF | 1.1 ± 0.1 |

The effect of each growth factor was determined from the mean of three experiments with the response being expressed as ratio to control. Errors are expressed as the standard error of the mean. In individual experiments, the response for each growth factor and the control was determined from the mean of three observations.
**Indicates that the mean was significantly different from the control. Statistical comparisons were made using the Newman-Keuls nonparametric test and a z value <0.05 was considered statistically significant.

In addition, many of the elongated cells separated from the central cell mass. The perimeter of the cell mass also expanded in wells containing KGF, but the change was not proliferation different from the control. The expansion in the KGF-containing wells appeared to be attributable to extensions of sheets of cells from the initial cell mass. No individual cells were found separated from the central cell mass. SC-HGF effects were not different from controls, where there was no extension of the cell mass beyond the origin. HB-EGF and DC-HGF induced morphologic changes and significantly stimulated motility of cells at the edge of the central island (Table 2).

Central masses of cells stained with methylene blue for the control and each growth factor indicated marked expansion of the central cell mass in the EGF containing wells. Central human corneal epithelial cell masses were stained with methylene blue in control, KGF, single-chain HGF, and EGF containing wells. Two central islands were studied for each growth factor and the control. Circumferential lines of cells were observed in three of the wells immediately following removal of the cloning cylinder. The latter cells remained separated from the central cell mass throughout the experiment and did not interfere with the interpretation of results. Results with heparin-binding EGF and double-chain HGF were similar to those with EGF.

In the KGF-containing wells some increase in the diameter of the central cell mass was noted. There was no change in the diameter of the cell mass in control wells or wells containing SC-HGF. HB-EGF and DC-HGF produced expansion of the central mass similar to EGF. Table 2 shows the results from three experiments for each growth factor.

IMMUNOSTAINING: Immunocytology for keratin K3 (K3) and the Ki-67 antigen (Ki-67) of cells at the edge and center of the corneal epithelial cell mass in the central well experiments after 2 weeks exposure to growth factors was performed. Controls, EGF; KGF; and single-chain HGF were used. Stained for f actin demonstrated cell morphology. There was diminished staining with AE5 or Ki-67 at the edge in EGF containing wells where elongated, migratory cells were predominate. Many of these cells were migrating beyond the cell mass, but are not stained well for either Ki-67 or keratin K3, and are barely detectable. Staining for AE5 in the periphery of the well containing single-chain HGF appeared to be decreased compared to the control in the photograph provided, but this difference was not consistent throughout the periphery of each of the HGF-exposed cell masses. Results with heparin-binding EGF and double-chain HGF were similar to those obtained with EGF. Central and edge photographs showed AE5 keratin K3 as a marker of cell differentiation and Ki-67 as a marker of proliferation for the control and each growth factor. Along with each AE5 and Ki-67 image f-actin staining showed the location and cell morphology. Prominent AE5 positive suprabasilar cells were noted centrally and at the edge in the control wells. Few Ki-67 positive cells were noted at the edge or in the center of the cell mass in control wells. Few AE5 positive cells were noted at the edge or centrally in wells that were exposed to EGF, including cells that had the elongated morphology at the edge, suggesting an inhibitory effect of EGF on differentiation. Ki-67 positive cells were numerous in the center of the cell mass in wells exposed to EGF.

In contrast, few cells at the peripheral edge of the expanding cell mass were Ki-67 positive in cultures with EGF-induced cells with the elongated morphology. In KGF-containing wells AE5 positive supranasal cells were prominent centrally and at the edge of the cell mass. AE5 staining in KGF-treated cells was somewhat diminished in the peripheral and central cell mass compared with the control. The difference was not, however, as marked as it was for EGF. Ki-67 positive cells were also increased at the edge and center of the cell mass in KGF-containing wells compared with the control. In SC-HGF-containing wells, AE5 positive supranasal cells were present centrally and at the edge of the cell mass. With SC-HGF the number of Ki-67 positive cells at the edge and center of the well did not consistently differ from the control, although the area appeared to show some increase.

In a repeat experiment no increase in Ki-67 staining compared with the control was observed with SC-HGF. Again, there was an apparent decrease in the AE5 staining in the periphery of cell masses in SC-HGF wells compared with the control, but the difference was variable. The effects of HB-EGF and DC-HGF were the same as those observed with EGF.

WESTERN BLOTTING FOR KERATIN K3: Western blotting confirmed that EGF inhibited expression of the differentiation marker keratin K3 detected with the AE5 antibody. As indicated by Coomassie blue stained insoluble proteins, the protein loading was similar for samples prepared from control, EGF-treated, and KGF-treated cells. AE5 staining, however, was notably diminished in the EGF-treated cells compared with the control or KGF-treated cells. Enolase levels in the soluble protein fraction did not differ between the control, EGF-treated, and KGF-treated cells. The Western blotting experiment was repeated and identical results were obtained for AE5 and enolase in repeat experiments in which the cells were incubated for 17 days.

Keratin K3 expression has been shown to increase as corneal epithelial cells terminally differentiate (Schermer, Galvin, and Sun, 1986). The results with EGF, HB-EGF, TGF alpha and DC-HGF indicated that these growth factors inhibited differentiation of corneal epithelial cells. Elongated cells that emerge in response to EGF, HB-EGF, TGF alpha, or DC-HGF exposure in areas of low cell density or at the edge of an isolated cell mass showed increased motility. It is clear in cultures plated at low density that elongated, motile epithelial cells are not present in significant numbers in control cultures or in cultures containing EGF, HB-EGF, TGF alpha, or DC-HGF prior to 4 to 7 days of growth factor exposure.

In the confluent island experiments, similar elongated, migratory cells appeared at the edge of islands exposed to EGF, HB-EGF, TGF alpha, and DC-HGF. Cells with the elongated, motile morphology express low levels of the differentiation marker keratin K3 (Schermer, Galvin, and Sun, 1986) and exhibit markedly diminished proliferation. Decreased proliferation in response to longer term exposure to EGF, HB-EGF, or DC-HGF was noted by cell counting in cultures plated at low cell density (FIG. 9) and at the edge of an island of cells where Ki-67 positive cells were markedly diminished. EGF, HB-EGF, or DC-HGF-exposed cells within the center of an island of cells also had decreased expression of keratin K3, but exhibited higher levels of proliferation than cells at the periphery of the cell mass. It appeared therefore that the EGF, HB-EGF, or DC-HGF motility versus proliferation responses may be modulated by cell-cell interactions.

Few, if any, cells with the elongated morphology were noted in the center of islands of EGF, HB-EGF, or DC-HGF-exposed cells. The inhibitory effect of EGF, HB-EGF, or DC-HGF on differentiation was observed at high or low cell density. Western blotting using cells maintained at high cell density confirmed that EGF decreased expression of the differentiation marker keratin K3 compared to control cultures or cultures maintained with KGF.

EGF inhibition of differentiation of corneal epithelial cells compared to KGF was similar to that noted for the two growth factors in skin keratinocytes (Marchese et al., 1990). Other studies have also reported EGF stimulation of corneal epithelial cell motility (Kruse and Tseng, 1993; Grant et al., 1992; Nakamura et al., 1991; Nishida et al., 1990). One study showed changes in morphology associated with increased motility and decreased differentiation of rabbit corneal epithelial cells in response to EGF in defined medium (Kruse and Tseng, 1993). The inventor is the first to show motility changes with DC-HCF and HB-EGF in corneal epithelial cells.

The time course over which cells developed EGF, HB-EGF, or DC-HGF-induced changes to a motile cell type in serum-free defined medium in vitro is expected to differ somewhat in vivo. Motility of epithelial cells in vitro is commonly noted in the first 6 to 24 hours after epithelial wounding. Cells utilized in the in vitro study had been trypsinized and cultured for 24 hours without serum or growth factors. Additionally, the cells were isolated from the effects of the tear film, underlying stromal fibroblasts, and other influences. However, it is expected that the effects of EGF, HB-EGF, and DC-HGF in vivo will be similar to those noted in vitro, because even with all the changes that the cells are exposed to in culture, these responses were noted after growth factor addition. Nevertheless, the time course of events may be different because the cells in vivo are likely to be in an optimal state to respond to these factors immediately after they are added to the surface.

The EGF induction of motility dominated over the proliferative effect of KGF in cultures plated at low cell density since motile cells emerged that were identical to those in cultures containing only EGF. The inventor has demonstrated EGF stimulation of corneal epithelial cell proliferation in serum-free defined medium (Wilson et al., 1993) where cells were exposed to the growth factor for only 5 days. Proliferation has also been observed by visual inspection of low cell density cultures containing EGF, HB-EGF, or DC-HGF during the first 5–6 days, but no increase in cell numbers was detected by cell counting after 2 to 3 weeks of exposure. There was a gradual, but obvious, decline in cell numbers after 6 to 8 days when the EGF, HB-EGF, or DC-HGF-induced change in epithelial cell morphology to the motile cell type became predominant. This decline in cell numbers was likely attributable to the normal death of a proportion of cells that occurs during culture along with diminished proliferation of the epithelial cells after the shift to the motile morphology. In the central epithelial island experiments, by contrast, a net increase in cell mass in response to EGF appeared to result from continued proliferation in the central area despite diminished cell division in the periphery where the motile cells appeared to predominate.

KGF and combination single-chain/double-chain HGF stimulated corneal epithelial cell proliferation in low density cultures. KGF also stimulated proliferation in the center of the island of epithelial cells. In contrast to EGF, HB-EGF, or DC-HGF, however, KGF stimulated proliferation at the periphery of the epithelial cell mass in the central epithelial island experiments. In addition, no change to a motile morphology was noted with KGF, HGF and KGF commonly function as paracrine mediators; they are produced by fibroblast-type cells and diffuse to affect surrounding epithelial cells via specific receptors (Wong et al., 1991).

HGF is identical to the scatter factor (Gherardi and Stoker, 1990), which has been shown to stimulate the dissociation and scattering of epithelial cells. HGF has also been shown to stimulate migration of human keratinocytes (Matsumoto et al., 1991). Now for the first time it is shown that HGF stimulates migration of corneal epithelial cells. Initially, HGF scattering or motility effects on corneal epithelial cells were not detected, despite detecting proliferation in earlier experiments with HGF. Formulations with pure single chain HGF did not stimulate proliferation of human corneal epithelial cells, but double chain HGF did have this effect. The effects of pure single chain EGF (obtained from Genentech, South San Francisco, Calif., were similar to EGF. In cultures at low density, there was an initial increase in cell proliferation followed by decreases in cell numbers as elongated, motile cells appeared in the culture. In central island experiments double-chain HGF produced effects similar to EGF; cells at the margin of the island changed to an elongated morphology, became motile, and had diminished proliferation. In addition, double-chain HGF inhibited differentiation of human corneal epithelial cells as monitored by immunocytologic evaluation of the expression of keratin K3.

No difference was noted in the expression of enolase in corneal epithelial cells incubated with EGF and KGF. The expression of enolase has been shown to be high in mitotically active basal epithelial cells and diminished in differentiated supranasal cells (Zieske et al., 1992). Apparently, diminished differentiation of corneal epithelial cells in response to EGF in a high cell density culture does not correlate with increased expression of enolase.

Proliferation, migration, and differentiation are likely to be alternative cellular states. Individual corneal epithelial cells may undergo a transition from cell division to migration and vice versa. However, once the epithelial cell undergoes terminal differentiation, it is unable to resume cell division or migration. The results herein suggest that exogenous EGF can stimulate migration and inhibit differentiation of corneal epithelial cells. It appears also that EGF can stimulate or have no effect on cell division in corneal epithelial cells depending on the environment of the cell. Cells that are in culture at low density or are at the periphery of an isolated cell mass are induced to migrate by exogenous EGF, while proliferation is diminished. The same type of cells at high cell density are stimulated to proliferate by exogenous EGF. The corneal epithelial cells at the periphery of the central island are analogous to cells at the margin of a corneal epithelial wound and, therefore it is likely that EGF and/or double-chain HGF have a role in promoting the migration of these cells during wound healing. Once a confluent layer of cells is reformed in the area of the epithelial wound the motile cells could resume proliferation and eventually the cells or their progeny would differentiate to reestablish a normal stratified corneal epithelium.

Heparin-binding EGF (BH-EGF) is a recently discovered variant of EGF which contains a heparin binding domain (Higashiyama et al., 1991). HB-EGF mediates its effects via the EGF receptor. The effects of HB-EGF were identical to EGF. While the heparin binding domain of HB-EGF did not affect the activity in culture, it may affect tissue localization, retention, and other factors that influence the function of the growth factor.

Cell proliferation, motility, and differentiation are important processes that occur during normal corneal maintenance and wound healing. Each of these processes is subject to temporal and spatial regulation. The inventor has demonstrated an important role for certain growth factors in modulating these responses.

EXAMPLE 4

This example outlines a procedure for the treatment of keratoconjunctivitis sicca, commonly known as dry eye syndrome, in affected individuals. This disorder is quite common and often debilitating.

A patient typically exhibits decreased vision and irritation while complaining of discomfort in the eye that is not alleviated by blinking or the use of saline drops. Diagnosis is typically made on the basis of observation of ocular surface staining with rose bengal. Other methods to confirm a diagnosis of keratoconjunctivitis sicca may be used such as increased tear osmolarity and increased tear film instability.

Treatment will constitute the administration of a solution of HGF, EGF, TGF alpha or HB-EGF on the order of about 50–500 ng/ml in physiological saline buffered to pH 7.0 with phosphage buffer. The solution will be applied as eyedrops, several drops in each eye, four times per day or as needed to relieve discomfort. The patient will be examined on a regular basis to monitor subjective symptoms of discomfort and objective bases including visual examination of the ocular surface to determine the presence of mucins and a tear film. Generally, monitoring will be at 2–6 week intervals. Alleviation of symptoms, as well as decreased rose bengal staining of the ocular surface, decreased tear osmolarity measured with an osmometer, and increased tear stability measured by tear breakup time would be detected with continued treatment.

REFERENCES

The references listed below are incorporated herein by reference to the extent they supplement, explain, provide a background for or teach methodology, techniques and/or compositions employed herein.

Attisano L., Wrana J. K., Cheifetz S., Massagu J. Novel activan receptors. Distinct genes and alternative mRNA splicing generate a repertoire of serine/threonine kinase receptors. *Cell.* 1992;68:97–108.

Bottaro D. P., Rubin J. S., Faletto D. L., Chan A. M. L., Kmiecik T. E., Vande Woude G. F., and Aaronson S. A.

Identification of the hepatocyte growth factor receptor as c-met proto-oncogene product. *Science.* 1991;251:802–804.

Bottaro D. P., Rubin J. S., Ron D., Finch P. W., Florio C., and Aaronson S. A. Characterization of the receptor for keratinocyte growth factor. *J. Biol. Chem.* 1990;265:12767–12770.

Brazzell R. K., Stern M. E., Aquavella J. V., Beuerman R. W., Baird L. Human recombinant epidermal growth factor in experimental corneal wound healing. *Invest. O., Pathalmol. Vis. Sci.* 1991;32:336–40.

Brogdon J. D., McLaughlin S. A., Brightman A. H., Helper L. C. Effect of epidermal growth factor on healing of corneal endothelial cells in cats. *Am. J. Vet. Res.* 1989;50:1237–43.

Chung J. H., Fagerholm P. Treatment of rabbit corneal alkali wounds with human epidermal growth factor. *Cornea.* 1989;8:122–8.

D'Aquila, Bechtel L., Videler J. A., Eron J., Gorczyca P., Kaplan J. C. Maximizing sensitivity and specificity of PCR by preamplification heating. *Nucleic Acid. Res.* 1991;19:3749.

Finch P. W., Rubin J. S., Miki T., Ron D., Aaronson S. A. Human KGF is FGF-related with properties of a paracrine effector or epithelial cell growth. *Science.* 1989;245:752–755.

Gherardi E. and Stoker M. Hepatocytes and Scatter factor. *Nature.* 1990;346:228.

Gospodarowicz D., Mescher A. L., Brown K. D., Birdwell C. R. The role of fibroblast growth factor and epidermal growth factor in the proliferative response of the corneal and lens epithelium. *Exp. Eye. Res.* 1977;25:631–49.

Joyce N. C., Matkin E. D., Neufeld A. H. Corneal endothelial wound closure in vitro. Effects of epidermal growth factor and/or indomethacin. *Invest. Ophthalmol. Vis. Sci.* 1989;30:1548–59. corneal endothelial cells Junquero D., Modat G., Coquelet C., Bonne C. Retinoid-induced potentiation of epidermal growth factor mitogenic effect on corneal endothelial cells. *Cornea.* 1990;9:41–4.

Kandarakis A. S., Page C., Kaufman H. E. The effect of epidermal growth factor on epithelial healing after penetrating keratoplasty in human eyes. *Am. J. Ophthalmol.* 1984;98:411–5.

Kitazawa T., Kinoshita S., Fujita K., Araki K., and others. The mechanism of accelerated corneal epithelial healing by human epidermal growth factor. *Invest. Ophthalmol. Vis. Sci.* 1990;31:1773–81.

Marchese C., Rubin J., Ron D., Faggioni A., Torrisi M. R., Messina A., Frati L., and Aaronson S. A. Human keratinocyte growth factor activity on proliferation and differentiation of human keratinocytes: differentiation response distinguishes keratinocyte growth factor from epidermal growth factor family. *J. Cell. Physiology* 1990;144:326–332.

Matsumoto K., Hashimoto K., Yoshikawa K., and Nakamura T. Marked stimulation of growth and motility of human keratinocytes by hepatocyte growth factor. *Exp. Cell. Res.* 1991;196:114–120.

Miki T., Bottaro D. P., Fleming T. P., Smith C. L., Burgess W. H., Chan A. M-L, Aaronson S. A. Determination of ligand-binding specificity by alternative splicing: two distinct growth factor receptors encoded by a single gene. *Proc. Natl. Acad. Sci.* 1992;89:246–250.

Mivechi N. F., Rosi J. J. Use of polymerase chain reaction to detect the expression of the Mr 70,000 heat shock genes in control or heat shock leukemic cells as correlated to their heat response. *Cancer Res.* 1990;50:2877.

Miyazawa K., Tsubouchi H., Naka D., Takahashi K., Okigaki M., Arakaki N., Nakayama H., Hirono S., Sakiyama O., Takahashi K., Gohda E., Daikuhara Y., Kitamura N. Molecular cloning and sequence analysis of cDNA for human hepatocyte growth factor. *Biochem. Biophys. Res. Commun.* 1989;163, 967–973.

Monteasano R., Matsumoto K., Nakamura T., and Orci L. Identification of a fibroblast-derived epithelial morphogen as hepatocyte growth factor. *Cell.* 1991;67:901–908.

Nakamura T., Nishizawa T., Hagiya M., Seki T., Shimonishi M., Sugimura A., Tashiro K., Shimizu S. Molecular cloning and expression of human hepatocyte growth factor. *Nature.* 1989;342:440–443.

Nayak S. K., Binder P. S. The growth of endothelium from human corneal rims in tissue culture. *Invest. Ophthalmol. Vis. Sci.* 1984;25:1213–6.

Neufeld A. H., Joyce N. C., and Jumblatt M. M. Composition for enhancing healing of corneal endothelial tissue Ng S-Y, Gunning P., Eddy R., Ponte P., Leavitt J., Shows T., Kedes L. Evolution of the functional human beta-actin gene and its multi-pseudogene family: Conservation of noncoding regions and chromosomal dispersion of pseudogenes. *Mol. Cell. Biol.* 1985;5:2720.

Niederkorn J. Y., Meyer D. R., Ubelaker J. E., Martin J. H. Ultrastructural and immunohistological characterization of the SIRC corneal cell line. *In Vitro Cell. Dev. Biol.* 1990;26:923.

Park M., Dean M., Kaul K., Braun M. J., Gonda M. A., Vande W. G. Sequence of MET protooncogene cDNA has features characteristic of the tyrosine kinase family of growth factor receptors. *Proc. Natl. Acad. Sci.* 1987;84:6379–6383.

Prat M., Narsimhan R. P., Crepaldi T., Nicotra M. R., Natali P. G., Comoglio P. M. The receptor encoded by the human c-Met oncogene is expressed in hepatocytes, epithelial cells, and solid tumors. *Int. J. Cancer.* 1991;49:323–328.

Raymond G. M., Jumblatt M. M., Bartels S. P., Neufeld A. H. Rabbit corneal endothelial cells in vitro: effects of epidermal growth factor. *Invest. Ophthalmol. Vis. Sci.* 1986;27:474–9.

Reim M., Busse S., Leber M., Schulz C. Effect of epidermal growth factor in severe experimental alkali burns. *Ophthalmic. Res.* 1988;20:327–31.

Rich L. F., Hatfield J. M., Louiselle I. The influence of epidermal growth factor on cat corneal endothelial wound healing. *Curr. Eye. Res.* 1991;10:823–30.

Rubin J. S., Chan A. M. L., Bottaro D. P., Burgess W. H., Taylor W. G., Cech A. C., Hirschfield D. W., Wong J., Miki T., Finch P. W., and Aaronson S. A. A broad-spectrum human lung fibroblast-derived mitogen is a variant of hepatocyte growth factor. *Proc. Natl. Acad. Sci. (USA).* 1991;88:415–419.

Rubin J. S., Osada H., Finch P. W., Taylor W. G., Rudikoff S., and Aaronson S. A. Purification and characterization of a newly identified growth factor specific for epithelial cells. *Proc. Natl. Acad. Sci. (USA)* 1989;86:802–806.

Soong H. K., Hassan T., Varani J., Huang S. C., Brennan M. Fibronectin does not enhance epidermal growth factor-mediated acceleration of corneal epithelial wound closure. *Arch. Ophthalmol.* 1989;107:1052–4.

Wilson S. E., He Y-G, Lloyd S. A. Epidermal growth factor, epidermal growth factor receptor, basic FGF, TGF beta-1, and IL-1 alpha messenger RNA production in human corneal epithelial cells and stromal fibroblasts. *Invest. Ophthalmol. Vis. Sci.* 1992;33:1756–1765.

Finch, P. W., Rubin, J. S., Miki, T., Ron, D. and Aaronson, S. A. (1989). Human KGF is FGF-related with properties of a paracrine effect or of epithelial cell growth. *Science*, 245:752–5.

Gerdes, J., Lemke, H., Baisch, H., Wacker, H. H., Schwab, U. and Stein, H. (1984). Cell cycle analysis of a cell proliferation-associated human nuclear antigen defined by the monoclonal antibody Ki-67, *J. Immunol.*, 133:1710–15.

Gerdes, J., Schwab, U., Lemke, H. and Stein, H. (1983). Production of mouse monoclonal antibody reactive with a human nuclear antigen associated with cell proliferation, *Int. J. Cancer*, 31:13–20.

Gherardi, E. and Stoker, M. (1990). Hepatoxytes and scatter factor, *Nature*, 346:228.

Grant, M. B., Khaw, P. T., Schultz, G. S., Adams, J. L. and Shimizu, R. W. (1992). Effects of epidermal growth factor, fibroblast growth factor, and transforming growth factor-beta on corneal cell-chemotaxis, *Invest. Ophthalmol. Vis. Sci.*, 33:3292–301.

Higashiyama, S., Abraham, J. A., Miller, J., Fiddes, J. C. and Klagbrun, M. (1991). A heparin-binding growth factor secreted by macrophage-like cells that is related to EGF, Science, 251:936–9.

Kruse, F. E. and Tseng, S. C. (1993). Growth factors modulate clonal growth and differentiation of cultured rabbit limbal and corneal epithelium, *Invest. Ophthalmol. Vis. Sci.*, 34:1963–76.

Marchese, C., Rubin, J., Ron, D., Raggioni, A., Torrisi, M. R., Messina, A., Frati, L. and Aaronson, S. A. (1990). Human keratinocyte growth factor activity on proliferation and differentiation of human keratinocytes: Differentiation response distinguishes KGF from EGF family, *J. Cell. Physiol.*, 144:326–332.

Matsumoto, K., Hashimoto, K., Yoshikawa, K. and Nakamura, T. (1991). Marked stimulation of growth and motility of human keratinocytes by hepatocyte growth factor, *Exp. Cell Res.*, 196:114–120.

Miyazawa, K., Shimomura, T., Kitamura, A., Kondo, J., Morimoto, Y. and Kitamura, N. (1993). Molecular cloning and sequence analysis of the cDNA for a human serine protease responsible for activation of hepatocyte growth factor. Structural similarity of the protease precursor to blood coagulation factor XII, *J. Biol. Chem.*, 15:10024–8.

Montesano, R., Matsumoto, K., Nakamura, T. and Orci, L. (1991). Identification of a fibroblast-derived epithelial morphogen as hepatocyte growth factor. *Cell*, 67:901–908.

Nakamura, M., Mishima, H., Nishida, T., and Otori, T. (1991). Requirements of microtubule assembly of initiation of EGF-stimulated corneal epithelial cell migration, *Jpn. J. Ophthalmol.*, 35:377–85.

Nishida, T., Nakamura, M., Mishima, H. and Otori, T. (1990). Differential mode of action of fibronectin and epidermal growth factor on rabbit corneal epithelial migration, *J. Cel. Physiol.*, 145:549–54.

Okashi, Y., Motokura, M., Kinoshita, Y., Mano, T., Wananabe, H., Kinoshita, S., Manabe, R., Oshiden, K. and Yanaihara, (1989). Presence of epidermal growth factor in human tears, *Invest. Ophthalmol. Vis. Sci.*, 30:1879–82.

Rubin, J. S., Chan, A. M. L., Bottaro, D. P., Burgess, W. H., Taylor, W. G., Cech, A. C., Hirschfield, D. W., Wong, J., Miki, T., Finch, P. W. and Aaronson, S. A. (1991). A broad-spectrum human lung fibroblast-derived mitogen is a variant of hepatocyte growth factor, *Proc. Natl. Acad. Sci. (USA)*, 88:415–9.

Rubin, J. S., Osada, H., Finch, P. W., Taylor, W. G., Rudikoff, S. and Aaronson, S. A. (1989). Purification and characterization of a newly identified growth factor for epithelial cells, *Proc. Natl. Acad. Sci. (USA)*, 86:802–6.

Sambrook, J., Fritsch, E. F. and Maniatis, T. (1989). Molecular cloning. A laboratory manual. Second edition, Cold Spring Harbor, Cold Spring Harbor Laboratory Press, pp. 18.60–18.74.

Schermer, A., Galvin, S., Sun, T-T. (1986). Differentiation-related expression of a major 64K corneal keratin in vivo and in culture suggests limbal location of corneal epithelial stem cells, *J. Cell Biol.*, 103:49–62.

Tsutsumi, O., Tsutsumi, A., and Oka, T. (1988). Epidermal growth factor-like, corneal wound healing substance in mouse tears, *J. Clin. Invest.*, 81:1067–71.

Wilson, S. E., He, Y-G. and Lloyd, S. A. (1992b). EGF, EGF receptor, basic FGF, TGF beta-1, and IL-1 alpha messenger RNA production in human corneal epithelial cells and stromal fibroblasts, *Invest. Ophthalmol. Vis. Sci.*, 33:1756–1765.

Wilson, S. E., Lloyd, S. A., He, Y-G. (1993). Fibroblast Growth Factor Receptor-1 Messenger RNA Expression in Corneal Cells, *Cornea.*, 12:249–54.

Wilson, S. E., Walker, J. W., Chwang, E. L., He, Y-G. (1993). Hepatocyte growth factor (HGF), keratinocyte growth factor (KGF), their receptors, FGF Receptor-2, and the cells of the cornea, *Invest. Ophthalmol. Vis. Sci.*, 34:2544–61.

Wong, S. T., Winchell, L. F., McCune, B. K. et al. (1989). The TGF-alpha precursor expressed on the cell surface binds to the EGF receptor on adjacent cells, leading to signal transduction, *Cell*, 56:495–506.

Zar, J. H. (1984). Biostatistical Analysis, Englewood Cliffs, N.J.: Prentice-Hall, Inc. pp. 188–190.

Zieske, J. D., Bukusoglu, G. and Yankauckas, M. A. (1992). Characterization of a potential marker of corneal epithelial stem cells, *Invest. Ophthalmol. Vis. Sci.*, 33:143–52.

Zieske, J. D., Bukusoglu, G., Yankauckas, M. A., Wasson, M. E. and Keulmann, H. T. (1992). Alpha-enolase is restricted to basal cells of stratified squamous epithelium, *Dev. Biol.*, 151:18–26.

What is claimed is:

1. A method of inhibiting corneal epithelial cell differentiation comprising contacting a corneal cell with an amount of a growth factor selected from the group consisting of hepatocyte growth factor (HGF) and keratinocyte growth factor (KGF) effective to inhibit corneal cell differentiation.

2. The method of claim 1 wherein the dry eye ocular disease is keratoconjunctivitis sicca.

3. The method of claim 1 wherein the cell is contacted sequentially with two growth factors from said group.

4. The method of claim 1 wherein the corneal cell is in a mammal.

5. The method of claim 4 wherein the corneal cell differentiation is associated with dry eye ocular disease.

6. The method of claim 5 wherein the dry eye ocular disease is further identified as keratoconjunctivitis sicca.

7. The method of claim 1 wherein the cell is contacted simultaneously with hepatocyte growth factor (HGF) and keratinocyte growth factor (KGF).

8. The method of claim 6 further including combining the growth factor with a timed release system.

9. The method of claim 8 wherein the timed release delivery system is a biodegradable polymer encapsulating the growth factor.

10. The method of claim 9 wherein the biodegradable polymer is a microcapsule.

11. The method of claim 5 further comprising topically administering the growth factor.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

CTCCTCCTC 9

( 2 ) INFORMATION FOR SEQ ID NO:2:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

GAAGTCCAGG GCGACGTAGC AC 22

( 2 ) INFORMATION FOR SEQ ID NO:3:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

AGTACTGTGC AATTAAAACA TGCG 24

( 2 ) INFORMATION FOR SEQ ID NO:4:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

TGGTCCTTTG GCGTCGTCCT C 21

( 2 ) INFORMATION FOR SEQ ID NO:5:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

GCCACACTAA CTATGGAAAA TG 22

( 2 ) INFORMATION FOR SEQ ID NO:6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

GGATCAAGCA CGTGGAAAAG A                                          21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GGATCAAGCA CGTGGAAAAG A                                          21

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GAAGTCCAGG GCGACGTAGC AC                                         22

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTGTTTGGGA TAAGTTGCCC A                                          21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CTCATCATCA GCGTTATCTT C                                          21

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TTCCAGGATT TGCTGGCCCA AGT                                        23

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GCCCTATATA ATTGGAGACC T                                              21

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ACCATGCAGA GTGAAAGGAT A                                              21

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CAGTTGTTTC CATAGGAACA TCAGTATCAT                                     30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CTTTAGGGTG CCAGCATTTT AGCATTACTT                                     30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CCATAGGAAA AAAGCATGAT TATTTGTGGG                                     30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GCCTCGGTCA CATTGAACAG AGCCAGCACT                                     30

( 2 ) INFORMATION FOR SEQ ID NO:18:

( i ) SEQUENCE CHARACTERISTICS:
        ( A ) LENGTH: 30 base pairs
        ( B ) TYPE: nucleic acid ( C ) STRANDEDNESS: single
( D ) TOPOLOGY: linear ( x i ) SEQUENCE DESCRIPTION: SEQ ID NO:18:

GTTACATTCC GAATATAGAG AACCTCAATC    30